United States Patent
Wang et al.

(10) Patent No.: US 10,688,412 B2
(45) Date of Patent: Jun. 23, 2020

(54) AFFINITY CHROMATOGRAPHY WASH BUFFER

(71) Applicant: Cephalon, Inc., Frazer, PA (US)

(72) Inventors: Lu Wang, West Chester, PA (US); Tianyi Zhou, West Chester, PA (US); Zhaoqing Zhang, West Chester, PA (US); Mi Jin, West Chester, PA (US)

(73) Assignee: Cehpalon, Inc., Frazer, PA (US)

( * ) Notice: Subject to any disclaimer, the term of this patent is extended or adjusted under 35 U.S.C. 154(b) by 218 days.

(21) Appl. No.: 15/659,093

(22) Filed: Jul. 25, 2017

(65) Prior Publication Data

US 2018/0021696 A1    Jan. 25, 2018

Related U.S. Application Data

(60) Provisional application No. 62/523,032, filed on Jun. 21, 2017, provisional application No. 62/366,309, filed on Jul. 25, 2016, provisional application No. 62/366,302, filed on Jul. 25, 2016.

(51) Int. Cl.
| | | |
|---|---|---|
| *B01D 15/38* | (2006.01) |
| *C07K 1/22* | (2006.01) |
| *C07K 14/555* | (2006.01) |
| *C07K 16/18* | (2006.01) |
| *C07K 16/28* | (2006.01) |

(52) U.S. Cl.
CPC ............ *B01D 15/3809* (2013.01); *C07K 1/22* (2013.01); *C07K 14/555* (2013.01); *C07K 16/18* (2013.01); *C07K 16/2875* (2013.01); *C07K 16/2896* (2013.01); *C07K 2317/56* (2013.01); *C07K 2319/74* (2013.01)

(58) Field of Classification Search
None
See application file for complete search history.

(56) References Cited

U.S. PATENT DOCUMENTS

| | | |
|---|---|---|
| 4,672,044 A | 6/1987 | Schreiber |
| 5,429,746 A | 7/1995 | Shadle et al. |
| 6,531,577 B1 | 3/2003 | Kaersgaard et al. |
| 8,497,358 B2 | 7/2013 | Suenaga et al. |
| 2005/0176109 A1 | 8/2005 | Yumioka et al. |
| 2006/0030696 A1 | 2/2006 | Bonnerjea et al. |
| 2006/0257972 A1 | 11/2006 | Ishihara |
| 2007/0054390 A1 | 3/2007 | Kelley et al. |
| 2007/0207500 A1 | 9/2007 | Nanying et al. |
| 2008/0064860 A1* | 3/2008 | Sun .................... C07K 1/16 530/413 |
| 2008/0064861 A1 | 3/2008 | Shujun |
| 2008/0312425 A1 | 12/2008 | Bonnerjea et al. |
| 2009/0162372 A1 | 6/2009 | King et al. |
| 2009/0318674 A1 | 12/2009 | Gagnon et al. |
| 2010/0063261 A1 | 3/2010 | Nanying et al. |
| 2010/0068215 A1 | 3/2010 | Seehra et al. |
| 2010/0136006 A1 | 6/2010 | Lin et al. |
| 2011/0105730 A1 | 5/2011 | Nanying et al. |
| 2019/0046956 A1 | 2/2019 | Wang et al. |

FOREIGN PATENT DOCUMENTS

| | | |
|---|---|---|
| EP | 0333474 A2 | 9/1989 |
| EP | 2182003 A1 | 5/2010 |
| EP | 2383336 A1 | 11/2011 |
| EP | 2583973 B1 | 3/2018 |
| JP | 5504579 B2 | 7/1993 |
| JP | 2009/522580 A | 2/2010 |
| WO | WO 92/07084 A1 | 4/1992 |
| WO | WO 2005/051994 A2 | 6/2005 |
| WO | WO 2006/023403 A2 | 3/2006 |
| WO | WO 2006/023420 A2 | 3/2006 |
| WO | WO 2007/081851 A2 | 7/2007 |
| WO | WO 2010/019493 A1 | 2/2010 |
| WO | WO 2010/056550 A1 | 5/2010 |
| WO | WO 2010/084851 A1 | 7/2010 |
| WO | WO 2009/025300 A1 | 11/2010 |
| WO | WO 2011/162210 A1 | 12/2011 |
| WO | WO 2018/170488 A1 | 9/2018 |

OTHER PUBLICATIONS

Connell-Crowley, L., et al. "Cation exchange chromatography provides effective retrovirus clearance for antibody purification processes," Biotechnol. Bioeng. 109:157-165, John Wiley & Sons, United States (2012).

GE Healthcare Life Sciences, "Process-scale Purification of Monoclonal Antibodies—Polishing using Capto™ Q," accessed at https://www.gelifesciences.com/gehcls_images/GELS/Related%20Content/Files/1314750913712/litdoc28903716_20161014161829.PDF in (2006).

Holstein et al., Protein A Intermediate Wash Strategies, BioProcess International, Feb. 6, 2015, [retrieved on Sep. 29, 2017, Accessed at [http://www.bioprocessintl.com/downstreamprocessing/chromatography/protein-intermediate-wash-strategies/] p. 1, para 1, p. 6.

(Continued)

*Primary Examiner* — Daniel E Kolker
*Assistant Examiner* — James L Rogers
(74) *Attorney, Agent, or Firm* — Sterne, Kessler, Goldstein & Fox P.L.L.C.

(57) ABSTRACT

A wash buffer comprising greater than 0 mM and less than about 500 mM arginine, greater than 0 mM and less than about 250 mM guanidine, greater than 0 mM and less than about 250 mM sodium chloride, and greater than 0 mM and less than about 50 mM of an anionic surfactant, or greater than 0% and less than about 0.25% w/v of a non-ionic surfactant. When used during affinity chromatography purification of a protein of interest, such as an antibody, the wash buffer significantly reduces the level of host cell proteins from the preparation. Following affinity chromatography with the wash buffer, the protein of interest may be further purified using membrane chromatography.

20 Claims, 7 Drawing Sheets

Specification includes a Sequence Listing.

(56) References Cited

OTHER PUBLICATIONS

Liu, H.F., et al., "Recovery and Purification Process Development for Monoclonal Antibody Production," mAbs 2(5):480-499, Taylor & Francis, United States (2010).

Miesegaes, G., et al., "Analysis of viral clearance unit operations for monoclonal antibodies," *Biotechnol. Bioeng.* 106:238-246, John Wiley & Sons, United States (2010).

Miesegaes, G., et al., "Monoclonal antibody capture and viral clearance by cation exchange chromatography," *Biotechnol. Bioeng.* 109:2048-2058, John Wiley & Sons, United States (2012).

Roguska, M.A., et al., "A Comparison of Two Murine Monoclonal Antibodies Humanized by CDR-grafting and Variable Domain Resurfacing," Protein Engineering 9(10):895-904, Oxford University Press, England (1996).

Shukla, A.A., et al., "Downstream Processing of Monoclonal Antibodies—Application of Platform Approaches," Journal of chromatography B 848(1):28-39, Elsevier, Netherlands (2007).

Thermo Fisher Scientific Inc. Instructions Pierce Protein Refolding Kit (2010) [retrieved on Oct. 14, 2017, Accessed at [https://assets.thermofisher.com/TFS-Assets/LSG/manuals/MAN0011490_Pierce_Protein_Refolding_UG.pdf,] p. 1, Description, Base Refolding Buffer 5, 6 and 8-9.

International Search Report and Written Opinion for International Application No. PCT/US2017/43743, International Search Authority, United States, dated Sep. 12, 2016, 16 pages.

Co-pending U.S. Appl. No. 16/014,778, inventors Wang, L., et al., filed Jun. 21, 2018.

Jungbauer; A. et al., "Pilot scale production of a human monoclonal antibody against human immunodeficiency virus HIV-1," J Biochem Biophys Methods 19(2-3):223-40, Elsevier, Netherlands (1989).

Arakawa; T. et al., "Elution of antibodies from a Protein-A column by aqueous arginine solutions," Protein Expression and Purification 36:244-248, Elsevier, Netherlands (2004).

Arakawa; T. et al., "The effects of arginine on protein binding and elution in hydrophobic interaction and ion-exchange chromatography," 54(1): 110-116 (2007).

Goebl; N.A. et al., "Neonatal Fc receptor mediates internalization of Fc in transfected human endothelial cells," Mol Biol Cell 19(12):5490-505, (2008).

Pingoud; A. et al., "Arbeitsmethoden der Biochemie," Walter de Gruyter p. 89-91, 214, (1997).

Koelsch; G. et al., "Aspartic Proteinases Advances in Experimental Medicine and Biology," Chapter 31, vol. 362, p. 275, Springer, New York (1995).

Vejaratpimol, R. et al., "Detection and Serological Relationships of Cymbidium Mosaic Potexvirus Isolates," Journal of Bioscience and Bioengineering 87(2):161-168, Elsevier, Netherlands (1999).

Ghose; S. et al., "Antibody variable region interactions with Protein A: Implications for the development of generic purification processes," Biotechnology and Bioengineering 92(6):665-673, Wiley Interscience, United States (2005).

Lebreton; G. et al., Purification Strategies to Process 5g/L Titers of Monoclonal Antibodies, Biopharm International, vol. 2009 supplement, Issue 2 (2009).

"Ion Exchange Chromatography & Chromatofocusing," p. 34, 35, 46, 47, 129-139, Amersham Bio-Sciences (2004).

Leaflet on CaptoAdhere, GE Healthcare Bio Sciences (2006).

Protein Purification Handbook, Amersham Biosciences p. 19-23 (2001).

Antibody Purification Handbook, GE Healthcare Bio-Sciences p. 5, 6, 47, 48, 66, 70, 92, 105 and 106 (2007).

International Search Report and Written Opinion, dated Sep. 20, 2011, issued by the International Searching Authority in corresponding International Application No. PCT/JP2011/064074.

Machine Translation of Description and Claims of U.S. Appl. No. 61/356,899.

English Translation of Application for WO 2010/084851, published Jul. 29, 2010.

English Translation of Application for WO 2009/025300, published Nov. 25, 2010.

Supplemental Partial European Search Report in EP Application No. 17835124, European Patent Office, Germany, dated Feb. 21, 2020, 15 pages.

* cited by examiner

| 1.  | Control |
|-----|---------|
| 2.  | 25 mM CA |
| 3.  | 25 mM CA, 150 mM NaCl |
| 4.  | 150 mM NaCl |
| 5.  | Triton + NaCl |
| 6.  | 0.1% Triton |
| 7.  | 0.05% Tributyle Pi |
| 8.  | 150 mM Guanidine, 150 mM NaCl |
| 9.  | 200 mM arginine, 150 mM NaCl |
| 10. | 50 mM Arginine |
| 11. | 200mM Arg, 0.05% Tributyle Pi, 150 mM NaCl |
| 12. | 250 mM Arginine, 25 mM CA, 150 mM NaCl |
| 13. | 100mM Arginine, 150 mM Guanidine, 25 mM CA, 150 mM NaCl |
| 14. | 0.1% Triton, 250mM Arginine, 150 mM NaCl |

AFFINITY CHROMATOGRAPHY WASH BUFFER

CROSS REFERENCE TO RELATED APPLICATIONS

This application relates to U.S. Provisional Application No. 62/366,302 filed on Jul. 25, 2016, U.S. Provisional Application No. 62/366,309 filed on Jul. 25, 2016, and U.S. Provisional Application No. 62/523,032, filed on Jun. 21, 2017, the contents of each of which are incorporated by reference herein, in their entirety and for all purposes.

REFERENCE TO A SEQUENCE LISTING SUBMITTED ELECTRONICALLY VIA EFS-WEB

The content of the electronically submitted sequence listing (Name: 2873_2740003_SeqListing.txt, Size: 8,311 bytes, and Date of Creation: Jul. 25, 2017) is herein incorporated by reference in its entirety.

BACKGROUND OF THE INVENTION

Field of the Invention

The invention relates generally to the field of protein biochemistry. More particularly, the invention relates to intermediate wash buffers used in affinity chromatography to purify target proteins from host cell proteins. Washing an affinity chromatography column with a basic amino acid, salt, anionic or non-ionic surfactant or organic phosphate, and guanidine, substantially reduces host cell protein impurities from the protein preparation.

Background Art

Recombinant proteins are expressed in host cells and purified by a series of chromatography and filtration steps (Liu et al., *MAbs* 2:5 480-499 (2010)). Protein A affinity chromatography is the most frequently used approach for monoclonal antibody purification due to its high specificity (Shukla et al., *J of Chrom. B* 848:1 28-39 (2007)). Host cell proteins (HCP), which are co-expressed with the target protein, are the major challenging impurities because HCP may be co-purified with the target proteins. Therefore, therapeutic-grade monoclonal antibodies (mAbs) are usually purified by Protein A chromatography followed by two or more polishing chromatographic steps to achieve desired purity of the protein of interest. Unfortunately, each additional chromatographic step inevitably reduces the protein yield as protein remains behind on the column. The use of additional columns increases the expense and operating complexity of the process.

A typical purification scheme, also known as a downstream cascade, employs affinity chromatography followed by cation exchange chromatography (CEX) or hydrophobic interaction chromatography (HIC) followed by anion exchange chromatography (AEX). Cation exchange chromatography and anion exchange are usually considered as polishing steps (See, e.g., GE Healthcare. (2006). Process-scale purification of monoclonal antibodies—polishing using Capto™ Q. www.gelifesciences.com/gehcls_images/GELS/Related %20Content/Files/1314750913712/litdoc28903716_20130507212449.PDF).

Reducing or eliminating polishing chromatographic steps by improving Protein A column performance can significantly reduce the development efforts and manufacturing cost, improve target product recovery as well as simplify manufacturing operations.

The present invention provides a comprehensive intermediate wash strategy applied onto an affinity chromatography column to improve the capture column performance, resulting in a reduced number of polishing steps needed. These data demonstrate that the mAb purification process can potentially be significantly simplified with the wash solution of the invention.

SUMMARY OF THE INVENTION

In a first aspect, the invention features an affinity chromatography wash solution, which comprises water, a basic amino acid, a salt and an anionic surfactant or non-ionic surfactant or organic phosphates. In some preferred embodiments, the basic amino acid is arginine, the salt is sodium chloride, and the anionic surfactant is sodium octanoate. In some preferred embodiments, the basic amino acid is arginine, the salt is sodium chloride, and the anionic surfactant is sodium octanoate, and the wash solution also comprises guanidine. In some preferred embodiments, the basic amino acid is arginine, the salt is sodium chloride, and the non-ionic surfactant is 4-(1,1,3,3-Tetramethylbutyl) phenyl-polyethylene glycol (TRITON® X-100). In some preferred embodiments, the basic amino acid is arginine, the salt is sodium chloride, and the organic phosphate is tributyl phosphate. The wash solution preferably has a pH range from 7-9. In a preferred embodiment, the wash solution has a pH of about 7.0, a pH of about 7.5, a pH of about 8.0, a pH of about 8.5, or a pH of about 9.0.

In some embodiments, the wash solution comprises greater than 0 mM and less than about 500 mM arginine, greater than 0 mM and less than about 300 mM sodium chloride, and greater than 5 mM and less than about 45 mM of an anionic surfactant. The wash solution may comprise from about 50 mM to about 150 mM arginine, from about 75 mM to about 125 mM arginine, from about 85 mM to about 115 mM arginine, from about 90 mM to about 110 mM arginine, from about 95 mM to about 105 mM arginine, from about 100 mM to about 400 mM arginine, from about 150 mM to about 350 mM arginine, from about 200 mM to about 300 mM arginine, from about 300 mM to about 350 mM arginine, or from about 250 mM to about 300 mM arginine. In some embodiments, the wash solution comprises about 300 mM arginine. In some embodiments, the wash solution comprises about 250 mM arginine. In some embodiments, the wash solution comprises about 200 mM arginine. In some embodiments, the wash solution comprises about 50 mM arginine, about 75 mM arginine, about 90 mM arginine, about 100 mM arginine, about 105 mM arginine, about 110 mM arginine, about 125 mM arginine, about 150 mM arginine, about 200 mM arginine, about 250 mM arginine, about 300 mM arginine, 350 mM arginine, about 400 mM arginine, about 450 mM arginine, or about 500 mM arginine.

In some embodiments, the wash may comprise from about 50 mM sodium chloride to about 200 mM sodium chloride, from about 100 mM sodium chloride to about 200 mM sodium chloride, from about 150 mM sodium chloride to about 200 mM sodium chloride, or from about 100 mM sodium chloride to about 150 mM sodium chloride. In some embodiments, the wash solution comprises about 200 mM sodium chloride. In some embodiments, the wash solution comprises about 50 mM sodium chloride, about 100 mM sodium chloride, or about 150 mM sodium chloride. In some embodiments, the wash solution comprises about 100 mM sodium chloride.

In some embodiments, the wash solution may comprise from about 5 mM to about 45 mM of the anionic surfactant, from about 10 mM to about 40 mM of the anionic surfactant, from about 20 mM to about 30 mM of the anionic surfactant, or from 22.5 mM to about 27.5 mM of the anionic surfactant. In some embodiments, the wash solution comprises from about 22.5 mM to about 27.5 mM of the anionic surfactant. In some embodiments, the wash solution comprises about 5 mM of the anionic surfactant, about 20 mM of the anionic surfactant, about 22.5 mM of the anionic surfactant, about 25 mM of the anionic surfactant, about 30 mM of the anionic surfactant, about 40 mM of the anionic surfactant or about 45 mM of the anionic surfactant. In some embodiments, the anionic surfactant comprises sodium octanoate.

In some embodiments, the wash solution comprises about 300 mM arginine, about 250 mM arginine, or about 200 mM arginine, and about 150 mM sodium chloride or about 100 mM sodium chloride, and about 25 mM of the anionic surfactant. In some embodiments, the wash solution comprises about 250 mM arginine, about 150 mM sodium chloride, and about 25 mM of an anionic surfactant such as sodium octanoate, and has a pH of about 7.5.

In some embodiments, the wash solution comprises greater than about 50 mM and less than about 150 mM arginine, greater than about 50 mM and less than about 250 mM guanidine, greater than 0 mM and less than about 300 mM sodium chloride, and greater than about 5 mM and less than about 45 mM of an anionic surfactant. The wash solution may comprise from about 50 mM to about 150 mM arginine, from about 75 mM to about 125 mM arginine, from about 85 mM to about 115 mM arginine, from about 90 mM to about 110 mM arginine, from about 95 mM to about 105 mM arginine, or from about 98 mM to about 102 mM arginine. In some embodiments, the wash solution comprises about 100 mM arginine. The wash solution may comprise from about 50 mM guanidine to about 200 mM guanidine, from about 50 mM guanidine to about 250 mM guanidine, from about 100 mM guanidine to about 200 mM guanidine, from about 150 mM guanidine to about 200 mM guanidine, from about 100 mM guanidine to about 150 mM guanidine, from about 125 mM guanidine to about 175 mM guanidine, from about 135 mM guanidine to about 165 mM guanidine, or from about 145 mM guanidine to about 155 mM guanidine. In some embodiments, the wash solution comprises about 150 mM guanidine. In some embodiments, the wash solution comprises about 100 mM arginine and about 150 mM guanidine. In some embodiments, the wash solution comprises about 50 mM guanidine, about 125 mM guanidine, about 135 mM guanidine, about 145 mM guanidine, about 150 mM guanidine, about 155 mM guanidine, about 160 mM guanidine, about 165 mM guanidine, about 170 mM guanidine, about 175 mM guanidine, about 180 mM guanidine, about 185 mM guanidine, about 190 mM guanidine, about 195 mM guanidine, about 200 mM guanidine. Such wash solutions may further comprise an anionic surfactant, may further comprise sodium chloride, or may further comprise an anionic surfactant and sodium chloride.

In some embodiments, the wash solution comprising arginine and guanidine comprises from about 5 mM to about 45 mM of the anionic surfactant, from about 20 mM to about 30 mM of the anionic surfactant, from about 22.5 mM to about 27.5 mM of the anionic surfactant, from about 22 mM to about 28 mM of the anionic surfactant, or from about 23 mM to about 29 mM of the anionic surfactant. In some embodiments, the wash solution comprises about 25 mM of the anionic surfactant. The anionic surfactant is preferably sodium octanoate. In some preferred embodiments, the wash solution comprises about 100 mM arginine, about 150 mM guanidine, and about 25 mM of an anionic surfactant, which preferably is sodium octanoate, and has a pH of about 7.5.

In some embodiments, the wash solution comprising arginine and guanidine or comprising arginine, guanidine, and anionic surfactant comprises from about 50 mM sodium chloride to about 200 mM sodium chloride, from about 100 mM sodium chloride to about 200 mM sodium chloride, from about 150 mM sodium chloride to about 200 mM sodium chloride, from about 100 mM sodium chloride to about 150 mM sodium chloride, from about 125 mM sodium chloride to about 175 mM sodium chloride, from about 135 mM sodium chloride to about 165 mM sodium chloride, or from about 145 mM sodium chloride to about 155 mM sodium chloride. In some embodiments, the wash solution comprises about 150 mM sodium chloride. In some preferred embodiments, the wash solution comprises about 100 mM arginine, about 150 mM guanidine, about 25 mM of an anionic surfactant, which preferably is sodium octanoate, and about 150 mM sodium chloride, and has a pH of about 7.5.

In some embodiments, the wash solution comprises greater than 0 mM and less than about 500 mM arginine, greater than 0 mM and less than about 250 mM sodium chloride, and greater than 0% and less than about 0.25% by volume of a non-ionic surfactant. The wash solution may comprise from about 100 mM to about 400 mM arginine, from about 150 mM to about 350 mM arginine, from about 200 mM to about 300 mM arginine, from about 300 mM to about 350 mM arginine, or from about 250 mM to about 300 mM arginine. In some embodiments, the wash solution comprises about 300 mM arginine. In some embodiments, the wash solution comprises about 250 mM arginine. In some embodiments, the wash solution comprises about 200 mM arginine. The wash may comprise from about 50 mM sodium chloride to about 200 mM sodium chloride, from about 100 mM sodium chloride to about 200 mM sodium chloride, from about 150 mM sodium chloride to about 200 mM sodium chloride, or from about 100 mM sodium chloride to about 150 mM sodium chloride. In some embodiments, the wash solution comprises about 200 mM sodium chloride. In some embodiments, the wash solution comprises about 150 mM sodium chloride. In some embodiments, the wash solution comprises about 100 mM sodium chloride. The wash solution may comprise from about 0.01% (w/v) to about 0.2% (w/v) of the non-ionic surfactant, from about 0.05% (w/v) to about 0.15% (w/v) of the non-ionic surfactant, from about 0.1% (w/v) to about 0.15% (w/v) of the non-ionic surfactant, or from about 0.05% (w/v) to about 0.1% (w/v) of the non-ionic surfactant. In some embodiments, the wash solution comprises about 0.01% (w/v), about 0.05% (w/v), about 0.1% (w/v), about 0.15% (w/v) or about 0.2% (w/v) of the non-ionic surfactant. In some embodiments, the non-ionic surfactant comprises TRITON® X-100. In some embodiments, the non-ionic surfactant comprises polysorbate 80.

In some embodiments, the wash solution comprises about 300 mM arginine, about 250 mM arginine, or about 200 mM arginine, and about 200 mM sodium chloride, about 150 mM sodium chloride, or about 100 mM sodium chloride, and about 0.0% of organic solvent. In some embodiments, the wash solution comprises about 250 mM arginine, about 150 mM sodium chloride, and about 0.1% (w/v) of a non-ionic surfactant, and has a pH of about 7.5.

In some embodiments, the wash solution comprises greater than 0 mM and less than about 500 mM arginine, greater than 0 mM and less than about 250 mM sodium chloride, and greater than 0% and less than about 0.1% by volume of an organic phosphate. The wash solution may comprise from about 100 mM to about 400 mM arginine, from about 150 mM to about 350 mM arginine, from about 200 mM to about 300 mM arginine, from about 300 mM to about 350 mM arginine, or from about 250 mM to about 300 mM arginine. In some embodiments, the wash solution comprises about 200 mM arginine. The wash may comprise from about 50 mM sodium chloride to about 200 mM sodium chloride, from about 100 mM sodium chloride to about 200 mM sodium chloride, from about 150 mM sodium chloride to about 200 mM sodium chloride, or from about 100 mM sodium chloride to about 150 mM sodium chloride. In some embodiments, the wash solution comprises about 200 mM sodium chloride. In some embodiments, the wash solution comprises about 150 mM sodium chloride. In some embodiments, the wash solution comprises about 100 mM sodium chloride. The wash solution may comprise from about 0.03% (w/v) to about 0.07% (w/v) of the organic phosphate. In some embodiments, the organic phosphate comprises tributyl phosphate.

In some embodiments, the wash solution increases viral clearance or inactivates viruses from a mixture containing the protein of interest. Viral clearance can be measured in $\log_{10}$ reduction values (LRV). In some embodiments, the wash solution increases viral clearance wherein the LRV is between about 1.0 and about 10.0 $\log_{10}$. In some embodiments, the wash solution increases viral clearance wherein the LRV is between about 1.0 $\log_{10}$ and about 5.0 $\log_{10}$, the LRV is between about 1.0 $\log_{10}$ and about 3.0 $\log_{10}$, the LRV is between about 2.0 $\log_{10}$ and about 4.0 $\log_{10}$, the LRV is between about 3.0 $\log_{10}$ and about 5.0 $\log_{10}$, the LRV is between about 3.0 $\log_{10}$ and about 8.0 $\log_{10}$, the LRV is between about 4.0 $\log_{10}$ and about 8.0 $\log_{10}$, or the LRV is between about 5.0 $\log_{10}$ and 6.0 $\log_{10}$. In some embodiments, the LRV is about 1.0 $\log_{10}$, the LRV is about 2.0 $\log_{10}$, the LRV is about 3.0 $\log_{10}$, the LRV is about 4.0 $\log_{10}$, the LRV is about 5.0 $\log_{10}$, the LRV is about 6.0 $\log_{10}$, the LRV is about 7.0 $\log_{10}$, the LRV is about 8.0 $\log_{10}$, the LRV is about 9.0 $\log_{10}$, or the LRV is about 10.0 $\log_{10}$.

Any such wash solutions may be used to purify proteins of interest using chromatography columns, such as protein A affinity, chromatography, cation exchange chromatography, hydrophobic interaction chromatography, or anion exchange chromatography. In a preferred embodiment, the chromatography column is a protein A chromatography column. In a preferred embodiment, the chromatography column is a cation exchange chromatography column. Compositions comprising purified proteins of interest, which proteins are, in some embodiments, purified according to the methods described or exemplified herein are provided. Thus, in another aspect, the disclosure features compositions. Such compositions comprise the protein of interest and a minimal amount of host cell proteins, the latter being co-expressed with the protein of interest but largely separated from the protein of interest via affinity chromatography using the described wash solutions. The proteins of interest preferably comprise antibodies. In some embodiments, the protein of interest is an antibody that specifically binds to TNF-like ligand 1A (TL1a). An antibody that specifically binds to TL1a may comprise a heavy chain variable region (VH) comprising the amino acid sequence of SEQ ID NO: 5 or SEQ ID NO: 6 and a light chain variable region (VL) comprising the amino acid sequence of SEQ ID NO: 7. In some embodiments, the protein of interest is an antibody that specifically binds to calcitonin gene-related peptide (CGRP). An antibody that specifically binds to CGRP may comprise a VH comprising the amino acid sequence of SEQ ID NO: 1 and a VL comprising the amino acid sequence of SEQ ID NO: 2. In some embodiments, the protein of interest is an antibody that specifically binds to CD38. An antibody that specifically binds to CD38 may comprise a VH comprising the amino acid sequence of SEQ ID NO: 3 and a VL comprising the amino acid sequence of SEQ ID NO: 4. An antibody that specifically binds to CD38 may further comprise a fusion to an interferon molecule, including an interferon alpha molecule, and including an attenuated interferon alpha molecule.

In some embodiments, a composition comprises an aqueous carrier, a recombinantly-expressed or hybridoma-expressed antibody that specifically binds to TL1a, and a level of host cell proteins that is less than about 500 ppm of the composition. In some preferred embodiments, the level of host cell proteins in the composition is less than about 450 ppm of the composition. In some preferred embodiments, the level of host cell proteins in the composition is less than about 300 ppm of the composition. In some preferred embodiments, the level of host cell proteins in the composition is less than about 200 ppm of the composition. In some preferred embodiments, the level of host cell proteins in the composition is less than about 150 ppm of the composition. In some preferred embodiments, the level of host cell proteins in the composition is less than about 100 ppm of the composition. ELISA may be used to determine the level (in ppm) of host cell proteins in the composition. The antibody may comprise a VH comprising the amino acid sequence of SEQ ID NO: 5 or SEQ ID NO: 6 and a VL comprising the amino acid sequence of SEQ ID NO: 7.

In some embodiments, a composition comprises an aqueous carrier, a recombinantly-expressed or hybridoma-expressed antibody that specifically binds to CGRP, and a level of host cell proteins that is less than about 800 ppm of the composition. In some preferred embodiments, the level of host cell proteins in the composition is less than about 700 ppm of the composition. In some preferred embodiments, the level of host cell proteins in the composition is less than about 500 ppm of the composition. In some preferred embodiments, the level of host cell proteins in the composition is less than about 200 ppm of the composition. In some preferred aspects, the level of host cell proteins in the composition is less than about 150 ppm of the composition. In some preferred embodiments, the level of host cell proteins in the composition is less than about 100 ppm of the composition. ELISA may be used to determine the level (in ppm) of host cell proteins in the composition. The antibody may comprise a VH comprising the amino acid sequence of SEQ ID NO: 1 and a VL comprising the amino acid sequence of SEQ ID NO: 2.

In some embodiments, a composition comprises an aqueous carrier, a recombinantly-expressed or hybridoma-expressed antibody that specifically binds to CD38 or a construct thereof comprising an interferon molecule fused to the antibody, and a level of host cell proteins that is less than about 500 ppm of the composition. In some preferred embodiments, the level of host cell proteins in the composition is less than about 400 ppm of the composition. In some preferred aspects, the level of host cell proteins in the composition is less than about 300 ppm of the composition. In some preferred embodiments, the level of host cell proteins in the composition is less than about 200 ppm of the composition. In some preferred embodiments, the level of host cell proteins in the composition is less than about 150 ppm of the composition. In some preferred embodiments, the level of host cell proteins in the composition is less than about 100 ppm of the composition. ELISA may be used to determine the level (in ppm) of host cell proteins in the composition. The antibody may comprise a VH comprising the amino acid sequence of SEQ ID NO: 3 and a VL comprising the amino acid sequence of SEQ ID NO: 4.

The wash solutions may be used in a protein purification method. In another aspect, the disclosure features methods for purifying a protein of interest, which is expressed from a cell, including by recombinant expression or by hybridoma expression. In general, the method comprises loading a mixture of a protein of interest and one or more contaminating host cell proteins onto an affinity chromatography ligand, washing the ligand with an aqueous wash solution comprising a basic amino acid, a salt, and a non-ionic surfactant or anionic surfactant to elute the one or more contaminant proteins from the ligand, and then eluting the protein of interest from the ligand, thereby forming a purified eluate of the protein of interest. The aqueous wash solution may be any such solution described or exemplified herein, including those wash solutions described in the preceding paragraphs. The ligand may be any suitable affinity ligand known to a person of ordinary skill in the art, for example, protein A wherein the protein of interest comprises an antibody. The method may further comprise expressing the protein of interest and one or more contaminant proteins in a bioreactor.

The method may further comprise acidifying (e.g., lowering the pH of) the purified eluate of the protein of interest to inactive viruses in the eluate. Lowering the pH is done for a period of time sufficient to inactivate viruses in the eluate, and then the pH is raised to a more neutral pH. The method may further comprise filtering the purified eluate of the protein of interest to remove viruses, including inactivated viruses. The method may further comprise treating the purified eluate of the protein of interest with diafiltration, ultrafiltration, or both diafiltration and ultrafiltration. The method may further comprise formulating the purified eluate of the protein of interest as a composition including a pharmaceutically acceptable excipient. The method may further comprise loading the purified eluate of the protein of interest onto a membrane chromatography support, for example, an anion exchange membrane chromatography support, and collecting flow through comprising a further-purified eluate from the membrane chromatography support. The method may further comprise formulating the further-purified eluate of the protein of interest as a composition including a pharmaceutically acceptable excipient.

In some aspects, the method does not comprise an anion exchange chromatography step. In some aspects, the method does not comprise a cation exchange chromatography step.

BRIEF DESCRIPTION OF THE DRAWINGS/FIGURES

DETAILED DESCRIPTION OF THE INVENTION

Figure 1:
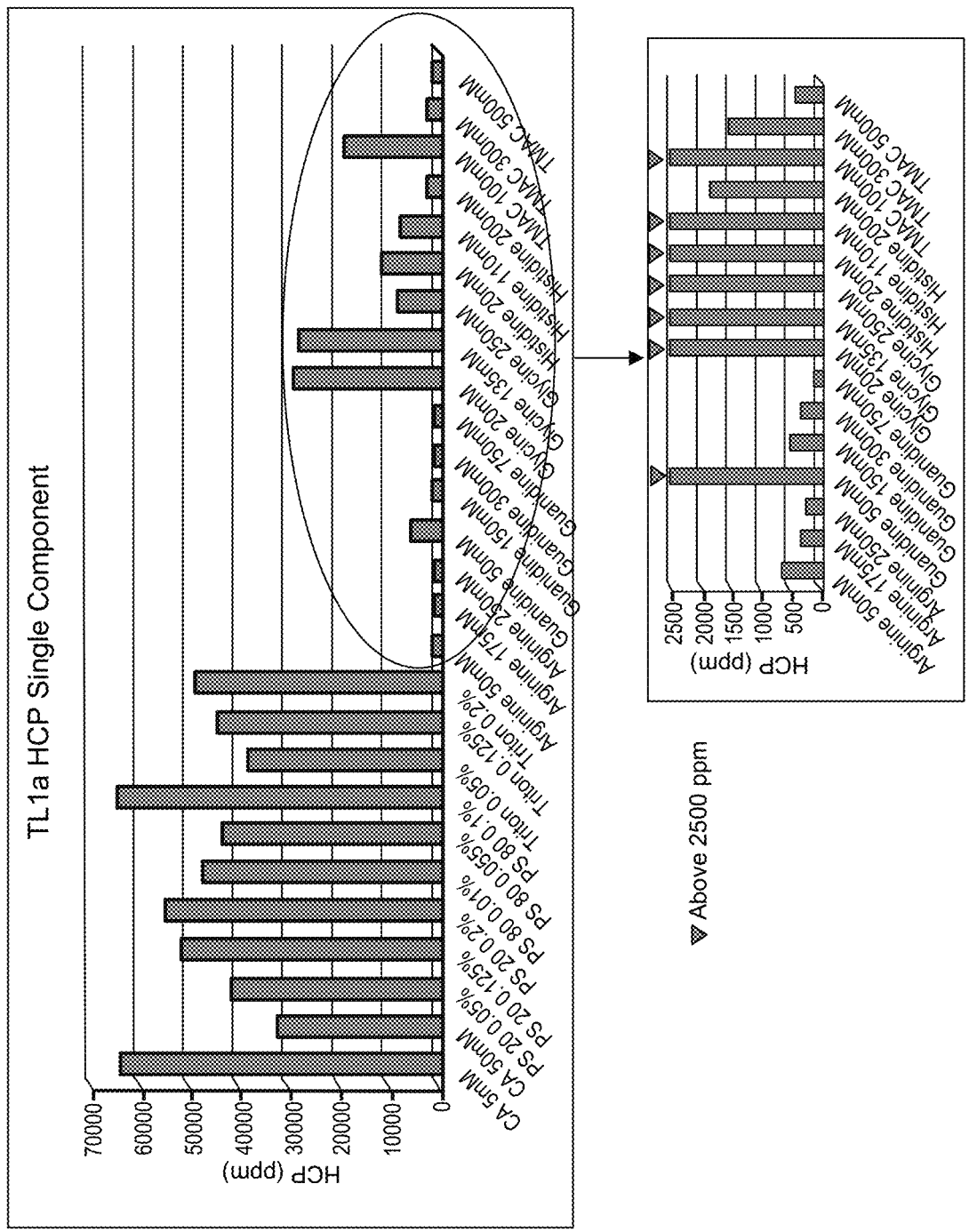
FIG. 1 shows HCP removal by single component wash buffers in resin plate.

Provided herein are affinity chromatography wash compositions, polypeptide purification schemes that utilize such compositions, and polypeptide preparations having a high degree of purity, for example, as having been purified with the use of such compositions or purification schemes.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "a solution comprising water" is used interchangeably with the term "an aqueous solution."

The terms "host cell proteins," "HCP," "host cell protein contaminants," and "host cell protein impurities" are used interchangeably herein.

The terms "polypeptide," "peptide," "polypeptide of interest" and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains. Preferably, the protein of interest is a polypeptide, an antibody, antigen binding fragment thereof, or an antibody construct.

The term "anti-TNF-like ligand 1A (TL1a)" refers to any protein capable of binding to TL1a. Anti-TL1a proteins include, for example anti-TL1a antibodies or antigen-binding fragments thereof.

The term "anti-calcitonin gene-related peptide (CGRP)" refers to any protein capable of binding to CGRP. Anti-GCRP proteins include, for example anti-CGRP antibodies or antigen-binding fragments thereof.

The term "anti-CD38" refers to any protein capable of binding to CD38. Anti-CD38 proteins include, for example anti-CD38 antibodies or antigen-binding fragments thereof.

As used herein, the terms "antibody" and "antibodies" are terms of art and can be used interchangeably herein and refer to a molecule with an antigen-binding site that specifically binds an antigen.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. As used herein, the term "antibody" encompasses bispecific and multispecific antibodies.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. An "antigen-binding fragment" can be a bispecific or multispecific antigen-binding fragment.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "hybridoma-expressed" refers to a protein of interest that is expressed in a hybrid cell line produced by the fusion of an immortal cell line of immunologic origin and an antibody producing cell. The term "hybridoma" encompasses progeny of heterohybrid myeloma fusions, which are the result of a fusion with human cells and a murine myeloma cell line subsequently fused with a plasma cell, commonly known as a trioma cell line. Furthermore, the term "hybridoma" is meant to include any immortalized hybrid cell line that produces antibodies such as, for example, quadromas (See, for example, Milstein et al., 1983, Nature, 537:3053). The hybrid cell lines can be of any species, including human and mouse.

The term "recombinantly-expressed" refers to a protein of interest is expressed in a "recombinant host cell" that has been genetically altered, or is capable of being genetically altered, by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell" as used herein.

The term "amino acid" refers to any naturally-occurring and/or non-natural amino acid residue. The term "naturally-occurring amino acid" refers to Ala, Arg, Asn, Asp, Cys, Glu, Gln, Gly, His, Ile, Leu, Lys, Met, Phe, Pro, Ser, Thr, Trp, Tyr, and Val. The term "basic amino acid" refers to arginine, lysine, glycine and histidine. Amino acids also include the D-forms of natural and non-natural amino acids. "D-" designates an amino acid having the "D" (dextrorotary) configuration, as opposed to the configuration in the naturally occurring ("L-") amino acids. Natural and non-natural amino acids can be purchased commercially (Sigma Chemical Co., Advanced Chemtech) or synthesized using methods known in the art.

The term "affinity chromatography" or "affinity purification" refers to a separation method based on a specific binding interaction between an ligand immobilized or coupled to a solid support and its binding partner. When a complex mixture is passed over the column, those molecules having specific binding affinity to the ligand become bound. After other sample components are washed away, the bound molecule is stripped form the support, resulting in its purification from the original mixture. Each specific affinity system requires its own set of conditions known to a person of ordinary skill in the art.

The term "affinity ligand" refers to metals (e.g., $Cd^{+2}$, $Co^{+2}$, $Cu^{+2}$, $Ga^{+3}$, $Fe^{+3}$, $Ni^{+2}$, and $Zn^{+2}$), dyes (e.g., Cibacron Blue and variants thereof), glutathione, subtilisin, Protein A, Protein G, Protein A/G, Protein L, boronate, avidin, streptavidin, biotin, anti-c-Myc, anti-HA, nucleotides, coenzymes, antibodies, heparin, antigens (especially for antibodies with a known specificity), and other known affinity ligands.

The term "viral clearance" is used interchangeably with the terms "viral inactivation", "inactivation of viruses", "virus removal" and "removal of viruses". The term "viral inactivation" includes rendering a virus contained in the mixture nonfunctional or removing a virus from the mixture to be purified. The virus may originate from the source of antibody production, downstream processing steps or manufacturing conditions. Methods of rendering a virus nonfunctional or removing a virus include heat activation, pH inactivation, chemical inactivating agents, etc. The term "pH viral inactivation" includes subjecting a virus to a pH sufficient to render the virus nonfunctional, e.g. a pH between about 2.5 and 5.0.

The terms "$\log_{10}$ reduction factor (LRF)," "$\log_{10}$ reduction value (LRV)," and "log clearance" are interchangeable and refer to the calculated ratio of the viral titer in the starting material and in the relevant product fraction. The reduction factor is a suitable parameter to describe the potential or capacity of a process step to remove or inactivate viruses. LRV of any process step can be measured using any known model virus that resembles viruses which may contaminate the product, e.g. murine leukemia virus (MuLV) and minute virus of mice (MVM).

The objective of viral clearance studies is to assess the process step(s) that can be considered to be effective in inactivating/removing viruses and to estimate quantitatively the overall level of virus reduction obtained by the process step(s). The level of virus reduction may be obtained by the addition ("spiking") of significant amounts of virus to the mixture containing the protein of interest, obtained after various process steps, and then demonstrating the removal or inactivation of the virus during subsequent steps. The reduction of virus infectivity may be achieved by the removal of virus particles or the inactivation of viral infectivity. Viral clearance studies are performed to demonstrate the clearance of a virus known to be present in the mixture. Reduction factors are normally expressed on a logarithmic scale (log 10). Model viruses for clearance evaluation studies are chosen to resemble viruses which may contaminate the mixture containing the protein of interest. Model viruses, such as xenotropic murine leukemia virus (X-MulV) and minute virus of mice (MVM), are often used for the viral clearance validation of cell line-derived proteins of interest.

In some embodiments, the wash solution increases viral clearance or inactivates viruses from a mixture containing the protein of interest. Viral clearance can be measured in log 10 reduction values (LRV). In some embodiments, the wash solution increases viral clearance wherein the LRV is between about 1.0 $\log_{10}$ and about 10.0 $\log_{10}$. In some embodiments, the wash solution increases viral clearance wherein the LRV is between about 1.0 $\log_{10}$ and about 5.0 $\log_{10}$, the LRV is between about 1.0 $\log_{10}$ and about 3.0 $\log_{10}$, the LRV is between about 2.0 $\log_{10}$ and about 4.0 $\log_{10}$, the LRV is between about 3.0 $\log_{10}$ and about 5.0 $\log_{10}$, the LRV is between about 3.0 $\log_{10}$ and about 8.0 $\log_{10}$, the LRV is between about 4.0 $\log_{10}$ and about 8.0 $\log_{10}$, or the LRV is between about 5.0 $\log_{10}$ and 6.0 $\log_{10}$. In some embodiments, the LRV is about 1.0 $\log_{10}$, the LRV is about 2.0 $\log_{10}$, the LRV is about 3.0 $\log_{10}$, the LRV is about 4.0 $\log_{10}$, the LRV is about 5.0 $\log_{10}$, the LRV is about 6.0 $\log_{10}$, the LRV is about 7.0 $\log_{10}$, the LRV is about 8.0 $\log_{10}$, the LRV is about 9.0 $\log_{10}$, or the LRV is about 10.0 $\log_{10}$.

The invention provides for a purified eluate and a composition comprising a protein of interest that is "substantially free" of viral particles as measured by viral clearance studies using any of the methods of the invention. As used herein, the term "substantially free of viral particles" refers to a purified eluate or composition comprising a protein of interest in which the protein of interest has been separated from viral particles. The term "substantially free" refers to a solution or composition comprising the protein of interest having less than about 0.0005% to about 0.001% viral particles. Preferably, the composition is "substantially free" when the composition has less than about 0.0005% viral particles.

The invention provides for a purified eluate and a composition comprising a protein of interest that is "free" of viral particles as measured by viral clearance studies using any of the methods of the invention. As used herein, the term "free of viral particles" refers to a composition having less than about 0.0001%. The composition is free of viral particles when the viral particles cannot be detected by viral clearance studies under conditions of maximum sensitivity.

It has been observed in accordance with the disclosure that the inclusion of both sodium chloride (NaCl) and a non-ionic surfactant or an anionic surfactant or organic phosphate with arginine in a wash solution substantially enhances the removal of host cell proteins (HCP) from a recombinant protein preparation during affinity chromatography purification. This enhancement in HCP removal was significant over each component by itself or in a combination with only one of the other components. The triple combination of the three components (1. arginine, NaCl and TRITON® X-100; 2. arginine, NaCl and sodium octanoate; or 3. arginine NaCl and tributyl phosphate) resulted in a greater than additive (e.g., synergistic) enhancement of HCP removal. It was further observed that the addition of guanidine allows for the use of relatively low concentrations of arginine, thus, potentially reducing the costs of the operation. Moreover, a low concentration (as compared to concentrations usually used within the art) of each of the components in the wash buffer still resulted in effective removal of HCP. This is advantageous because it potentially reduces environmentally unfriendly waste products. HCP (ppm) can be determined using the CHO Host Cell Proteins 3rd Generation kit (Immunoenzymetric Assay for the Measurement of CHO Host Cell Proteins, Catalog # F550, Cygnus Technologies, Southport, N.C.) following manufacturer's protocol.

The high degree of host cell protein removal from the combination of salt with non-ionic surfactant was unexpected because these excipients can have opposing effects, namely, that salt enhances hydrophobic interactions and non-ionic surfactants reduce hydrophobic interactions.

The high degree of host cell protein removal from the combination of arginine with anionic surfactant was also unexpected because the other uses of wash buffers in which arginine was combined with a surfactant, e.g., sodium octanoate (also called sodium caprylate or CA), lead to higher levels of HCP remaining as compared to using arginine alone in a wash buffer. See, e.g., Nabila et al. (2014) Biotechnol. Progress, 30:1114-24.

The combination of arginine and guanidine can significantly reduce the amount of each component used. U.S. Pat. No. 8,350,013 discloses effective impurity removal was generally observed with high concentrations of arginine, in particular >500 mM arginine or >1 M guanidine. In the present invention, the combination of 100 mM guanidine and 100 mM arginine achieved equivalent effective impurity removal. Arginine is expensive, and high concentrations of guanidine (around 1M guanidine) are corrosive. Therefore, the present invention can result in significant cost savings as well as resolving corrosion whilst achieving effective HCP removal.

The level of HCP removal was observed to be so substantial that subsequent purification steps with anion exchange (AEX) or cation exchange (CEX) chromatography could be removed from the protein purification scheme. The double step of AEX and CEX in the purification scheme can be replaced with a single step in the purification scheme of membrane chromatography to provide highly purified protein preparations. Viewed in isolation, the step of membrane chromatography is not as effective a purification step as compared to the combination of AEX and CEX (AEX+CEX). However, the affinity chromatography method of the present invention improves the purification process. The level of purification achieved by affinity chromatography and membrane affinity chromatography as described or exemplified herein is comparable to the level of purification achieved by affinity chromatography with the combination of AEX+CEX as exemplified in the prior art.

Replacement of AEX+CEX with membrane chromatography is advantageous, particularly for production of early phase clinical material, because membrane chromatography has a higher loading capacity and convective flow mass transfer, which translates to higher production throughput, reduction of buffer consumption and cost savings as compared to AEX or CEX resin-based purification process schemes. Furthermore, membrane chromatography is a disposable system which provides for more flexibility in a purification scheme as compared to column chromatography.

The disclosure features affinity chromatography wash compositions, polypeptide purification schemes that utilize such compositions, and polypeptide preparations having a high degree of purity, for example, as having been purified with the use of such compositions or purification schemes. The compositions and purification schemes are particularly well-suited for hybridoma- or recombinantly-expressed monoclonal antibodies, but may also be used in the preparation of any recombinantly expressed polypeptide purified by affinity chromatography.

The expression of a polypeptide of interest may be carried out in any suitable host cell, which may be transformed with a gene encoding the polypeptide. Host cells may be eukaryotic or prokaryotic, and include without limitation, bacteria cells, yeast cells, insect cells, and mammalian cells. Mammalian cells are preferred. Non-limiting examples of suitable mammalian cells include antibody-expressing hybridoma cells, as well as expression hosts such as Chinese Hamster Ovary (CHO) cells, human embryonic kidney 293 (HEK 293) cells, and murine hybridoma NS0 cells. The polypeptide expression may be secreted from the cell to the cell culture media, or may be within the cell. The cell culture may be in a bioreactor (e.g., fermentation). Typical bioreactor cell cultures are initiated with a basal medium, with nutrients periodically infused after culture initiation and until the completion of the culture. This infusion is generally of a feed medium, and sustains the cell culture during the protein expression phase. For the most part, feed medium infusion is carried out via a bolus infusion, with concentrated feed medium quickly added into the cell culture at set time points, usually once per day. Alternatively to a bolus feed, bioreactor cell cultures may be infused using an extended or a continuous feed. Commercially available feed media are suitable for bioreactor nutrient infusion.

The bioreactor may have a capacity of at least about 250 liters. In some aspects, the bioreactor has a capacity of at least about 500 liters. In some aspects, the bioreactor has a capacity of at least about 2000 liters. In some aspects, the bioreactor has a capacity of at least about 5000 liters, or 10,000 liters or 15,000 liters.

Following expression, the media containing the polypeptide (e.g., cell culture media) may be clarified, for example, to remove the host cells and particulate debris. Clarification may comprise filtration, centrifugation, or a combination thereof. For example, depth filtration through diatomaceous earth and cellulose fibers may be used. Membrane filtration, using any commercially available membrane filter, for example through a 0.2 µm filter, may be employed to remove any microbial contaminants.

Following expression, and clarification if employed, the polypeptide of interest may be purified via affinity chromatography to remove contaminating host cell proteins (HCPs). Affinity chromatography may include any affinity ligands suitable for purification of the polypeptide of interest. Non-limiting examples of affinity chromatography ligands include metals (e.g., $Cd^{+2}$, $Co^{+2}$, $Cu^{+2}$, $Ga^{+3}$, $Fe^{+3}$, Ni and $Zn^{+2}$), dyes (e.g., Cibacron Blue and variants thereof), glutathione, subtilisin, Protein A, Protein G, Protein A/G, Protein L, boronate, avidin, streptavidin, biotin, anti-c-Myc, anti-HA, nucleotides, coenzymes, antibodies, heparin, antigens (esp. for antibodies with a known specificity), and other known affinity ligands. The affinity ligand is generally immobilized on a solid support, for which there are numerous known and common supports. The support preferably comprises particles, e.g., beads, that may be packed into a chromatography column.

When Protein A and/or Protein G is used as an affinity chromatography ligand to purify an antibody or antibody construct, the antibody or antibody construct comprises an Fc domain, or at least the portion of an Fc domain that binds to a Protein A or Protein G ligand. The Fc domain or portion thereof is preferably of an IgG isotype, including any sub-type thereof capable of binding to Protein A or Protein G. When Protein L is used as an affinity chromatography ligand to purify an antibody or antibody construct, the antibody or antibody construct comprises a light (L) chain, or at least the portion of a light chain that binds to a Protein L ligand.

The polypeptide preparation is loaded onto the ligand-support, whereby the protein of interest non-covalently interacts with the ligand with sufficient affinity to bind to the ligand-support. The ligand preferably has a high protein-binding capacity. For example, a protein A ligand preferably has an antibody binding capacity of from about 10 g/L to about 100 g/L, and in some aspects has an antibody binding capacity of from about 10 g/L to about 60 g/L, and in some aspects has an antibody binding capacity of from about 20 g/L to about 50 g/L. The support is preferably equilibrated prior to loading with the polypeptide preparation. Equilibration is preferably with a buffer solution.

Loading of the polypeptide preparation onto the affinity chromatography support is carried out at a temperature, in a volume, and for a time suitable to allow adsorption of the polypeptide of interest to the ligand. Undesired HCPs that do not adsorb to the ligand flow through the support during chromatography.

In some preferred aspects, the polypeptide of interest comprises an antibody or antibody construct comprising a constant region, which is capable of interacting with Protein A. Thus, an expressed antibody preparation may be loaded onto a support comprising Protein A, whereby the antibodies interact with the Protein A ligand. The Protein A may have an antibody binding capacity of from about 10 g/L to about 100 g/L. Protein A supports are commercially available, including protein A affinity media (MABSELECT SURE®, GE Healthcare Life Sciences, Uppsala, Sweden), protein A affinity media (MABSELECT®, GE Healthcare Life Sciences, Uppsala, Sweden), protein A affinity media (MABSELECT SURE® LX, GE Healthcare Life Sciences, Uppsala, Sweden), protein A resin (UNOsphere SUPrA™, BioRad, Hercules, Calif.), protein A resin (ESHMUNO® A, Millipore Sigma, Billerica, Mass.), protein A resin (PO-ROS™ MABCAPTURE® A, Life Technologies Corp., Carlsbad, Calif.), protein A resin (AMSPHERE™ A3 support, JSR Life Sciences, Sunnyvale, Calif.), protein A resin (KANEKA KanCap™ A, (Osaka, Japan), protein A resin (PROSEP® Ultra Plus, Millipore Sigma, Billerica, Mass.), and silica-based protein A media (ABSOLUTE® High Cap, Novasep, Boothwyn, Pa.). Any suitable Protein A support available in the art may be used. Loading of an antibody preparation onto the Protein A support is carried out at a temperature, in a volume, and for a time suitable to allow for adsorption of the monoclonal antibodies to the Protein A ligand. Undesired HCPs that do not adsorb to the Protein A ligand flow through the support during chromatography.

To further remove HCPs that adhere to the affinity ligand or adhere to the polypeptide of interest, the polypeptide-adsorbed support is washed. The wash comprises an aqueous solution comprising a basic amino acid, a salt, and a non-ionic surfactant or an anionic surfactant. In preferred embodiments, the amino acid is arginine, though histidine, lysine, or glycine may be used in place of arginine. In some preferred embodiments, urea or guanidine may be used in place of or in combination with the amino acid (e.g., in place of or in combination with arginine, histidine, lysine, or glycine). In preferred embodiments, the salt is sodium chloride, though sodium sulfate, sodium phosphate, potassium phosphate, sodium citrate, or sodium acetate may be used in place of sodium chloride. In preferred embodiments, the non-ionic surfactant is TRITON® X-100 non-ionic surfactant, or polysorbate (e.g., TWEEN® brand non-ionic surfactants, J. T. Baker, N.J.), though NP-40, polysorbate 20, polysorbate 80, poloxamers, tri(n-butyl)phosphate (TNBP), tetramethylammonium chloride (TMAC), or sodium cholate may be used in place of TRITON® X-100. In preferred embodiments, the anionic surfactant, if used in place of a non-ionic surfactant, is sodium octanoate (also known as sodium caprylate). A preferred wash comprises arginine, sodium chloride, and TRITON® X-100 non-ionic surfactant. Another preferred wash comprises arginine, guanidine, sodium chloride, and sodium octanoate. Another preferred wash comprises arginine, sodium chloride, and sodium octanoate anionic surfactant. Sodium heptanoate, sodium nonanoate, sodium alkyl sulfates, sodium alkyl sulfonates, or N-Lauroylsarcosine may be used in place of sodium octanoate. Such wash solutions, as described and exemplified throughout this specification, are featured in accordance with the disclosure.

In some aspects, the wash solution preferably comprises water, arginine, sodium chloride, and sodium octanoate as an anionic surfactant, and the arginine is preferably at a concentration of greater than 0 mM and less than about 500 mM, the sodium chloride is preferably at a concentration of greater than 0 mM and less than about 250 mM, and the sodium octanoate is preferably at a concentration of greater than 0 mM and less than about 50 mM. In some embodiments, the wash solution comprises arginine, sodium chloride, and sodium octanoate, and the arginine is at a concentration of greater than 0 mM and less than about 400 mM, the sodium chloride is at a concentration of greater than 0 mM and less than about 200 mM, and the sodium octanoate is preferably at a concentration of greater than 0 mM and less than about 35 mM. In some embodiments, the wash solution comprises arginine, sodium chloride, and sodium octanoate, and the arginine is at a concentration of greater than 0 mM and less than about 350 mM, the sodium chloride is at a concentration of greater than 0 mM and less than about 200 mM, and the sodium octanoate is preferably at a concentration of greater than 0 mM and less than about 30 mM.

In some embodiments, the wash solution comprises arginine, sodium chloride, and sodium octanoate, and the arginine is at a concentration of greater than 0 mM and about 300 mM or less, the sodium chloride is at a concentration of greater than 0 mM and about 175 mM or less, and the sodium octanoate is preferably at a concentration of greater than 0 mM and about 30 mM or less. In some embodiments, the wash solution comprises arginine, sodium chloride, and sodium octanoate, and the arginine is at a concentration of greater than 0 mM and about 300 mM or less, the sodium chloride is at a concentration of greater than 0 mM and about 175 mM or less, and the sodium octanoate is preferably at a concentration of greater than 0 mM and about 25 mM or less. In some embodiments, the wash solution comprises arginine, sodium chloride, and sodium octanoate, and the arginine is at a concentration of greater than 0 mM and about 300 mM or less, the sodium chloride is at a concentration of greater than 0 mM and about 150 mM or less, and the sodium octanoate is preferably at a concentration of greater than 0 mM and about 25 mM or less. In some embodiments, the wash solution comprises arginine, sodium chloride, and sodium octanoate, and the arginine is at a concentration of greater than 0 mM and about 250 mM or less, the sodium chloride is at a concentration of greater than 0 mM and about 150 mM or less, and the sodium octanoate is preferably at a concentration of greater than 0 mM and about 25 mM or less.

In some embodiments, the wash solution comprises from about 100 mM to about 500 mM of arginine, from about 50 mM to about 250 mM of sodium chloride, and from about 10 mM to about 50 mM sodium octanoate. The wash solution may comprise from about 100 mM to about 400 mM of arginine, from about 50 mM to about 300 mM of sodium chloride, and from about 10 mM to about 40 mM sodium octanoate. The wash solution may comprise from about 150 mM to about 350 mM of arginine, from about 100 mM to about 300 mM of sodium chloride, and from about 15 mM to about 35 mM sodium octanoate. The wash solution may comprise from about 200 mM to about 300 mM of arginine, from about 200 mM to about 300 mM of sodium chloride, and from about 15 mM to about 35 mM sodium octanoate. The wash solution may comprise from about 250 mM to about 300 mM of arginine, from about 125 mM to about 175 mM of sodium chloride, and from about 20 mM to about 30 mM sodium octanoate. The wash solution may comprise from about 250 mM to about 300 mM of arginine, from about 150 mM to about 200 mM of sodium chloride, and from about 25 mM to about 30 mM sodium octanoate. The wash solution may comprise from about 200 mM to about 250 mM of arginine, from about 100 mM to about 150 mM of sodium chloride, and from about 20 mM to about 25 mM sodium octanoate. The wash solution may comprise from about 200 mM to about 250 mM of arginine, from about 100 mM to about 150 mM of sodium chloride, and from about 25 mM to about 30 mM sodium octanoate. The wash solution may comprise from about 225 mM to about 275 mM of arginine, from about 125 mM to about 175 mM of sodium chloride, and from about 20 mM to about 30 mM sodium octanoate. The wash solution may comprise from about 240 mM to about 260 mM of arginine, from about 140 mM to about 160 mM of sodium chloride, and from about 22 mM to about 28 mM sodium octanoate. The wash solution may comprise from about 245 mM to about 255 mM of arginine, from about 145 mM to about 155 mM of sodium chloride, and from about 24 mM to about 26 mM sodium octanoate. In some preferred embodiments, the wash solution comprises about 250 mM of arginine, about 150 mM of sodium chloride, and about 25 mM sodium octanoate.

In another aspect, the wash solution comprises water, arginine, and guanidine. In some embodiments, the wash solution further comprises an anionic surfactant. In some embodiments, the wash solution further comprises sodium chloride. In some embodiments, the wash solution further comprises an anionic surfactant and sodium chloride. The anionic surfactant may be sodium octanoate. Sodium heptanoate, sodium nonanoate, sodium alkyl sulfates, sodium alkyl sulfonates, or N-Lauroylsarcosine may be used in place of sodium octanoate.

In some embodiments, the wash solution comprises greater than 0 mM and less than about 200 mM arginine, greater than 0 mM and less than about 300 mM guanidine, greater than 0 mM and less than about 250 mM sodium chloride, and greater than 0 mM and less than about 50 mM of an anionic surfactant. In some embodiments, the wash solution comprises from about 50 mM to about 150 mM arginine, from about 75 mM to about 125 mM arginine, from about 85 mM to about 115 mM arginine, from about 90 mM to about 110 mM arginine, from about 95 mM to about 105 mM arginine, or from about 98 mM to about 102 mM arginine. In some embodiments, the wash solution comprises about 100 mM arginine. In some embodiments, the wash solution comprises from about 50 mM guanidine to about 200 mM guanidine, from about 100 mM guanidine to about 200 mM guanidine, from about 150 mM guanidine to about 200 mM guanidine, from about 100 mM guanidine to about 150 mM guanidine, from about 125 mM guanidine to about 175 mM guanidine, from about 135 mM guanidine to about 165 mM guanidine, or from about 145 mM guanidine to about 155 mM guanidine. In some embodiments, the wash solution comprises about 150 mM guanidine. In some embodiments, the wash solution comprises about 100 mM arginine and about 150 mM guanidine.

In some embodiments, the wash solution comprises from about 10 mM to about 40 mM of the anionic surfactant, from about 20 mM to about 30 mM of the anionic surfactant, from about 22.5 mM to about 27.5 mM of the anionic surfactant, from about 22 mM to about 28 mM of the anionic surfactant, or from about 23 mM to about 29 mM of the anionic surfactant. In some embodiments, the wash solution comprises about 25 mM of the anionic surfactant. The anionic surfactant is preferably sodium octanoate. In some preferred embodiments, the wash solution comprises about 100 mM arginine, about 150 mM guanidine, and about 25 mM of an anionic surfactant, which preferably is sodium octanoate, and has a pH of about 7.5.

In some embodiments, the wash solution comprises from about 50 mM sodium chloride to about 200 mM sodium chloride, from about 100 mM sodium chloride to about 200 mM sodium chloride, from about 150 mM sodium chloride to about 200 mM sodium chloride, from about 100 mM sodium chloride to about 150 mM sodium chloride, from about 125 mM sodium chloride to about 175 mM sodium chloride, from about 135 mM sodium chloride to about 165 mM sodium chloride, or from about 145 mM sodium chloride to about 155 mM sodium chloride. In some embodiments, the wash solution comprises about 150 mM sodium chloride. In some preferred embodiments, the wash solution comprises about 100 mM arginine, about 150 mM guanidine, about 25 mM of an anionic surfactant, which preferably is sodium octanoate, and about 150 mM sodium chloride, and has a pH of about 7.5.

In another aspect, the wash solution comprises water, a basic amino acid optionally in combination with guanidine, a salt and a non-ionic surfactant. More preferably, the wash solution comprises arginine, sodium chloride, and TRITON® X-100 non-ionic surfactant, and the arginine is preferably at a concentration of greater than 0 mM and less than about 500 mM, the sodium chloride is preferably at a concentration of greater than 0 mM and less than about 250 mM, and the TRITON® X-100 non-ionic surfactant is preferably at a concentration of greater than 0% and less than about 0.25% by volume. In some embodiments, the wash solution comprises arginine, sodium chloride, and TRITON® X-100 non-ionic surfactant, and the arginine is at a concentration of greater than 0 mM and less than about 400 mM, the sodium chloride is at a concentration of greater than 0 mM and less than about 200 mM, and the TRITON® X-100 non-ionic surfactant is at a concentration of greater than 0% and less than about 0.25% by volume. In some embodiments, the wash solution comprises arginine, sodium chloride, and TRITON® X-100 non-ionic surfactant, and the arginine is at a concentration of greater than 0 mM and less than about 350 mM, the sodium chloride is at a concentration of greater than 0 mM and less than about 150 mM, and the TRITON® X-100 non-ionic surfactant is at a concentration of less than about 0.2% by volume.

In some embodiments, the wash solution comprises arginine, sodium chloride, and TRITON® X-100 non-ionic surfactant, and the arginine is at a concentration of greater than 0 mM and about 300 mM or less, the sodium chloride is at a concentration of greater than 0 mM and about 100 mM or less, and the TRITON® X-100 non-ionic surfactant is at a concentration of about 0.15% or less by volume. In some embodiments, the wash solution comprises arginine, sodium chloride, and TRITON® X-100 non-ionic surfactant, and the arginine is at a concentration of greater than 0 mM and about 300 mM or less, the sodium chloride is at a concentration of greater than 0 mM and about 200 mM or less, and the TRITON® X-100 non-ionic surfactant is at a concentration of about 0.11% or less by volume. In some embodiments, the wash solution comprises arginine, sodium chloride, and TRITON® X-100 non-ionic surfactant, and the arginine is at a concentration of greater than 0 mM and about 300 mM or less, the sodium chloride is at a concentration of greater than 0 mM and about 150 mM or less, and the TRITON® X-100 non-ionic surfactant is at a concentration of about 0.1% or less by volume. In some embodiments, the wash solution comprises arginine, sodium chloride, and TRITON® X-100 non-ionic surfactant, and the arginine is at a concentration of greater than 0 mM and about 250 mM or less, the sodium chloride is at a concentration of greater than 0 mM and about 150 mM or less, and the TRITON® X-100 non-ionic surfactant is at a concentration of about 0.1% or less by volume.

In some embodiments, the wash solution comprises from about 100 mM to about 500 mM of arginine, from about 50 mM to about 250 mM of sodium chloride, and from about 0.01% to about 0.25% (w/v) of TRITON® X-100 non-ionic surfactant. The wash solution may comprise from about 100 mM to about 400 mM of arginine, from about 50 mM to about 200 mM of sodium chloride, and from about 0.01% to about 0.2% (w/v) of TRITON® X-100 non-ionic surfactant. The wash solution may comprise from about 150 mM to about 350 mM of arginine, from about 50 mM to about 200 mM of sodium chloride, and from about 0.01% to about 0.2% (w/v) of TRITON® X-100 non-ionic surfactant. The wash solution may comprise from about 100 mM to about 300 mM of arginine, from about 100 mM to about 200 mM of sodium chloride, and from about 0.05% to about 0.15% (w/v) of TRITON® X-100 non-ionic surfactant. The wash solution may comprise from about 200 mM to about 300 mM of arginine, from about 100 mM to about 200 mM of sodium chloride, and from about 0.05% to about 0.15% (w/v) of TRITON® X-100 non-ionic surfactant. The wash solution may comprise from about 250 mM to about 300 mM of arginine, from about 100 mM to about 150 mM of sodium chloride, and from about 0.05% to about 0.15% (w/v) of TRITON® X-100 non-ionic surfactant. The wash solution may comprise from about 300 mM to about 350 mM of arginine, from about 100 mM to about 150 mM of sodium chloride, and from about 0.1% to about 0.2% (w/v) of TRITON® X-100 non-ionic surfactant. The wash solution may comprise from about 250 mM to about 350 mM of arginine, from about 75 mM to about 125 mM of sodium chloride, and from about 0.1% to about 0.2% (w/v) of TRITON® X-100 non-ionic surfactant. The wash solution may comprise from about 275 mM to about 325 mM of arginine, from about 90 mM to about 110 mM of sodium chloride, and from about 0.1% to about 0.2% (w/v) of TRITON® X-100 non-ionic surfactant. The wash solution may comprise from about 290 mM to about 310 mM of arginine, from about 95 mM to about 105 mM of sodium chloride, and from about 0.13% to about 0.17% (w/v) of TRITON® X-100 non-ionic surfactant. The wash solution may comprise from about 295 mM to about 305 mM of arginine, from about 97 mM to about 103 mM of sodium chloride, and from about 0.14% to about 0.16% (w/v) of TRITON® X-100 non-ionic surfactant. The wash solution may comprise from about 298 mM to about 302 mM of arginine, from about 98 mM to about 102 mM of sodium chloride, and from about 0.14% to about 0.16% (w/v) of TRITON® X-100 non-ionic surfactant. The wash solution may comprise from about 299 mM to about 301 mM of arginine, from about 99 mM to about 101 mM of sodium chloride, and from about 0.14% to about 0.16% (w/v) of TRITON® X-100 non-ionic surfactant.

In some preferred embodiments, the wash solution comprises about 300 mM of arginine, about 100 mM of sodium chloride, and about 0.15% (w/v) of TRITON® X-100 non-ionic surfactant. In some preferred embodiments, the wash solution comprises about 200 mM of arginine, about 150 mM of sodium chloride, and about 0.15% (w/v) of TRITON® X-100 non-ionic surfactant. In some preferred embodiments, the wash solution comprises about 250 mM of arginine, about 100 mM of sodium chloride, and about 0.05% (w/v) of TRITON® X-100 non-ionic surfactant. In some preferred embodiments, the wash solution comprises about 300 mM of arginine, about 150 mM of sodium chloride, and about 0.05% (w/v) of TRITON® X-100 non-ionic surfactant. In some preferred embodiments, the wash solution comprises about 300 mM of arginine, about 200 mM of sodium chloride, and about 0.1% (w/v) of TRITON® X-100 non-ionic surfactant. In some preferred embodiments, the wash solution comprises about 250 mM of arginine, about 150 mM of sodium chloride, and about 0.1% (w/v) of TRITON® X-100 non-ionic surfactant. In some preferred embodiments, the wash solution comprises about 200 mM of arginine, about 100 mM of sodium chloride, and about 0.1% (w/v) of TRITON® X-100 non-ionic surfactant. In some preferred embodiments, the wash solution comprises about 250 mM of arginine, about 200 mM of sodium chloride, and about 0.15% (w/v) of TRITON® X-100 non-ionic surfactant. In some preferred embodiments, the wash solution comprises about 200 mM of arginine, about 200 mM of sodium chloride, and about 0.05% (w/v) of TRITON® X-100 non-ionic surfactant.

The conductivity target of the wash may range from about 15 mS/cm to about 45 mS/cm. The conductivity target of the wash may range from about 16 mS/cm to about 42 mS/cm, or from about 17 mS/cm to about 40 mS/cm, or from about 18 mS/cm to about 38 mS/cm. Conductivity target can be measured according to any suitable technique, including a conductivity meter.

In an embodiment, the wash solution comprises guanidine, arginine and NP40.

In an embodiment, the wash solution comprises guanidine, arginine and PS20.

In an embodiment, the wash solution comprises guanidine, arginine and caprylic acid (CA).

In an embodiment, the wash solution comprises Tributyl phosphate and arginine.

In an embodiment, the wash solution comprises Tributyl phosphate, arginine, and a salt, such as NaCl.

In an embodiment, the wash solution comprises TRITON® X-100 and arginine.

Optionally, the wash solution also comprises salt, such as NaCl.

In an embodiment, the wash solution comprises 200 mM aarginineinine, 0.05% tributyl Pi, 150 mM NaCl.

In an embodiment, the wash solution comprises 250 mM arginine, 25 mM CA, 150 mM NaCl.

In an embodiment, the wash solution comprises 100 mM arginine, 150 mM guanidine, 25 mM CA, 150 mM NaCl.

In an embodiment, the wash solution comprises 100 mM arginine, 150 mM guanidine, 25 mM CA, 150 mM NaCl.

In an embodiment, the wash solution comprises 250 mM arginine+0.1% w/v TRITON® X-100 (or +0.05% w/v tributyl phosphate).

In an embodiment, the wash solution comprises 50-100 mM arginine+100-250 mM guanidine+25 mM CA, preferably with >50 mM arginine, and with >100 mM guanidine.

In an embodiment, the wash solution comprises 0.15% w/v TRITON® X-100 non-ionic surfactant, 300 mM arginine and 100 mM NaCl.

In an embodiment, the wash solution comprises 0.05%-0.15% w/v TRITON® X-100, 200-300 mM arginine and 100-200 mM NaCl.

In an embodiment, the wash solution comprises 100 mM arginine, 150 mM guanidine, 25 mM CA, 150 mM NaCl.

In an embodiment, the wash solution comprises 200 mM arginine, 0.05% w/v tributyl, 150 mM NaCl.

In an embodiment, the wash solution comprises 250 mM arginine, 150 mM NaCl, 0.1% w/v TRITON In an embodiment, the wash solution comprises 350 mM guanidine+0.05% w/v tributyl.

In an embodiment, the wash solution comprises 0.1% w/v TRITON® X-100, 250 mM arginine, 150 mM NaCl In an embodiment, the wash solution comprises 25 mM caprylic acid, 100 mM arginine, 150 mM guanidine and 150 mM NaCl.

In an embodiment, the wash solution comprises 25 mM CA, 250 mM arginine, and 150 mM NaCl.

In an embodiment, the wash solution comprises 25 mM caprylic acid, 350 mM guanidine and 150 mM NaCl.

In an embodiment, the wash solution comprises 25 mM caprylic acid, 100 mM arginine, 100 mM guanidine and 150 mM NaCl.

In an embodiment, the wash solution comprises 25 mM caprylic acid, 100 mM arginine, 250 mM guanidine and 150 mM NaCl.

In an embodiment, the wash solution comprises 25 mM caprylic acid, 50 mM arginine, 100 mM guanidine and 150 mM NaCl.

In an embodiment, the wash solution comprises 25 mM caprylic acid, 50 mM arginine, 250 mM guanidine and 150 mM NaCl.

In an embodiment, the wash solution comprises 0.05% w/v Tributyl phosphate, 250 mM arginine and 150 mM NaCl.

In an embodiment, the wash solution comprises 0.05% w/v Tributyl phosphate, 350 mM arginine and 150 mM NaCl.

In one embodiment, the was solution comprises 0.05% w/v Tributyl phosphate, 200 mM arginine and 150 mM NaCl.

In an embodiment, the wash solution comprises 350 mM guanidine and 150 mM NaCl.

In an embodiment, the wash solution comprises 0.05% w/v TRITON® X-100, 200 mM arginine and 200 mM NaCl.

In an embodiment, the wash solution comprises 0.15% w/v TRITON® X-100, 250 mM arginine and 200 mM NaCl.

In an embodiment, the wash solution comprises 0.1% w/v TRITON® X-100, 200 mM arginine and 100 mM NaCl.

In an embodiment, the wash solution comprises 0.1% w/v TRITON® X-100, 250 mM arginine and 150 mM NaCl.

In an embodiment, the wash solution comprises 0.1% w/v TRITON® X-100, 300 mM arginine and 200 mM NaCl.

In an embodiment, the wash solution comprises 0.05% w/v TRITON® X-100, 300 mM arginine and 150 mM NaCl.

In an embodiment, the wash solution comprises 0.05% w/v TRITON® X-100, 250 mM arginine and 100 mM NaCl.

In an embodiment, the wash solution comprises 0.15% w/v TRITON® X-100, 300 mM arginine and 100 mM NaCl.

In an embodiment, the wash solution comprises 0.15% w/v TRITON® X-100, 200 mM arginine and 150 mM NaCl.

The wash solutions described and exemplified herein are used to wash an affinity chromatography column toward the removal of contaminants, including HCP. Following washing, the polypeptide of interest is eluted from the affinity ligand. The elution buffer is generally tailored to the type of affinity ligand and, accordingly, may vary. Elution may be carried out at a temperature, in a volume, and for a time suitable to allow for maximal elution yield of the protein of interest. Elution of the polypeptide produces an affinity chromatography eluate comprising the polypeptide. In aspects where the polypeptide comprises an antibody or antibody construct comprising a constant region and in which the affinity ligand is Protein A, the elution buffer is preferably acidic. Elution of the antibody or antibody construct produces an affinity chromatography eluate comprising the antibody or antibody construct.

In an embodiment, the method of the invention comprises: (i) loading a mixture containing the peptide of interest (e.g. the antibody) and impurities (e.g. HCP) onto the protein A chromatography column; (ii) washing the column with the wash solution of the invention to reduce the level of HCP in the mixture and increase the purity of the antibody (such as to create a purified antibody); and (iii) applying an elution buffer to the column to release the chromatography elute. The affinity chromatography elute comprises a mixture of purified antibody with a reduced level of HCP as compared to the mixture that was loaded onto the protein A chromatography column in step (i).

The affinity chromatography eluate comprising the polypeptide, including the eluate comprising the antibody or antibody construct, includes a substantially reduced level of host cell proteins (HCP), which proteins were removed from the preparation of the polypeptide via such wash solutions during affinity chromatography. The affinity chromatography eluate comprising the polypeptide, including the eluate comprising the antibody or antibody construct, preferably comprises less than about 1000 ppm of host cell proteins. HCP values in parts per million (ppm) may also be expressed as ng of HCP per mg of product. In some embodiments, the affinity chromatography eluate comprises less than about 900 ppm of host cell proteins. In some embodiments, the affinity chromatography eluate comprises less than about 800 ppm of host cell proteins. In some embodiments, the affinity chromatography eluate comprises less than about 700 ppm of host cell proteins. In some embodiments, the affinity chromatography eluate comprises less than about 600 ppm of host cell proteins. In some embodiments, the affinity chromatography eluate comprises less than about 500 ppm of host cell proteins. In some embodiments, the affinity chromatography eluate comprises less than about 400 ppm of host cell proteins. In some embodiments, the affinity chromatography eluate comprises less than about 350 ppm of host cell proteins. In some embodiments, the affinity chromatography eluate comprises less than about 300 ppm of host cell proteins. In some embodiments, the affinity chromatography eluate comprises less than about 250 ppm of host cell proteins. In some embodiments, the affinity chromatography eluate comprises less than about 200 ppm of host cell proteins. In some embodiments, the affinity chromatography eluate comprises less than about 150 ppm of host cell proteins. In some embodiments, the affinity chromatography eluate comprises less than about 100 ppm of host cell proteins. The amount of host cell proteins (e.g., in ppm), can be determined according to any suitable assay, including an ELISA such as a quantitative host cell protein ELISA. For example, the ppm of HCP are as measured by an ELISA assay. Liquid chromatography-mass spectrometry (LC-MS) may also be used to measure, as well as characterize the HCP. HCP ELISA kits are commercially available (e.g., CHO HCP ELISA kit (Cygnus Technologies, Southport, N.C. 28461, USA, cat # F550)), and any such kits are suitable for measuring HCP content.

As well as reducing the HCP content, the affinity chromatography wash solutions of the invention may be used to reduce the level of viruses or to inactivate viruses in the composition containing the protein of interest. Typical prior art purification processes use anion exchange followed by a further acidification treatment to reduce the level of viruses or to inactivate viruses during protein (e.g. antibody) purification methods. Surprisingly, the present inventors have found that use of an affinity chromatography wash solution of the present invention reduces the level of viruses sufficiently to omit the step of anion exchange chromatography.

The affinity chromatography eluate (e.g., comprising the polypeptide or comprising the antibody or antibody construct) may be further treated with cation exchange method and/or a treatment to inactivate any residual viruses present in the eluate. The virus inactivation may comprise acidifying the eluate at a temperature and for a period of time sufficient to inactivate any viruses present in the eluate. The acidification may comprise, for example, adding acetic acid, citric acid, hydrochloric acid, formic acid, or combination thereof to the eluate until a desired pH is achieved. After low pH viral inactivation, the eluate may be neutralized to pH 5.0 to 7.5 (depend on process needs). During the neutralization step, turbidity may appear in the product pool due to precipitation of impurities (or product). Depth filtration may be used to filter the pH-adjusted preparation to remove turbidity as well as impurities.

Following virus inactivation, or following elution from the affinity chromatography if virus inactivation is not included, or following the cation exchange step if it is included, the polypeptide of interest may be further purified with membrane chromatography. The affinity chromatography eluate, which includes a purified polypeptide of interest, which may comprise an antibody or antibody construct, typically is pH adjusted and loaded onto a membrane chromatography support and allowed to flow through the membrane, whereby remaining host cell protein contaminants bind to the membrane and the protein of interest remains in the flow-through. The membrane chromatography flow-through (which is still the affinity chromatography eluate containing the purified polypeptide of interest) comprises the polypeptide of interest and less host cell proteins than were in the affinity chromatography eluate before being loaded onto the chromatography membrane. The membrane chromatography support may comprise an anion exchange membrane, such as SARTOBIND® Q (Sartorius AG, Goettingen, Germany), MUSTANG® Q (Pall Corp., Westborough, Mass.), NATRIX® HDQ (Natrix, Burlington, Ontario, Canada), or a salt-tolerant multi-module anion-exchange membrane, such as a SARTOBIND® STIC membrane (Sartorius AG, Goettingen, Germany), or CHROMASORB membranes (Millipore Sigma, Billerica, Mass.). Thus, membrane chromatography may comprise anionic exchange membrane chromatography. The membrane chromatography step can typically remove from about 50% to about 99% or more of the remaining impurities.

Figure 7:
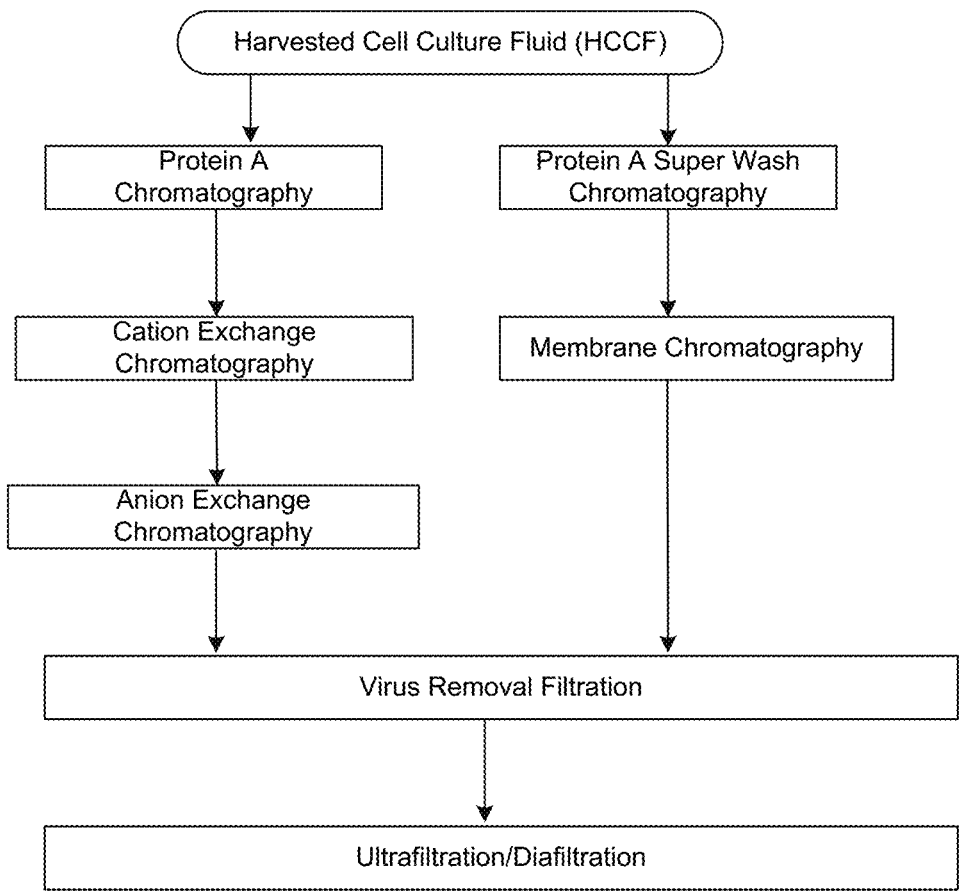
FIG. 7 shows a flow chart of a traditional antibody purification scheme (left column) compared against a new purification scheme (right column) utilizing the Protein A wash buffers of the invention, with membrane chromatography following Protein A chromatography.

The affinity chromatography eluate contains a purified polypeptide of interest, which may comprise an antibody or antibody construct. As indicated above, the affinity chromatography eluate may be further processed in order to inactivate any extant viruses, and/or may be further purified via a second chromatography step such as membrane chromatography or cation exchange chromatography. In any case, whether the affinity chromatography eluate is treated for virus inactivation or further purified, the resulting composition of the polypeptide of interest, including an antibody or antibody construct, may be further processed into a form suitable for therapeutic administration, for example, to an non-human animal or to a human being. Such further processing may include any combination of ultrafiltration, nanofiltration, concentration, and diafiltration of the purified preparation of the polypeptide of interest (FIG. 7).

Ultrafiltration is a process for concentrating the preparation of the polypeptide of interest. Proteins are filtered from other molecules in solution based on the membrane pore size or molecular weight cutoff. Diafiltration is used to exchange the polypeptide of interest into a desired buffer (e.g., from an elution buffer into a stable formulation buffer). Ultrafiltration and diafiltration typically employ tangential flow filtration.

Following a purification scheme, which includes the use of an affinity chromatography wash buffer of the present invention, and which scheme optionally further includes one or more of a second chromatography purification step (e.g., membrane chromatography and/or cation exchange in any order), and which scheme optionally further includes virus inactivation, nanofiltration, ultrafiltration, and/or diafiltration, the polypeptide of interest is preferably present in a composition. The composition preferably includes a carrier and the polypeptide of interest. The carrier is preferably aqueous, and may be a pharmaceutically acceptable carrier. The carrier may comprise a buffer, and may comprise one or more pharmaceutically acceptable excipients. The composition may be referred to as a pharmaceutical composition. The terms "composition" and "purified composition" are used interchangeably herein.

The composition comprising the polypeptide of interest, including an antibody or antibody construct, preferably comprises less than about 1000 ppm of host cell proteins. The composition preferably comprises less than about 900 ppm of host cell proteins, less than about 800 ppm of host cell proteins, less than about 700 ppm of host cell proteins, less than about 600 ppm of host cell proteins, less than about 500 ppm of host cell proteins, less than about 450 ppm of host cell proteins, less than about 400 ppm of host cell proteins, less than about 350 ppm of host cell proteins, less than about 300 ppm of host cell proteins, less than about 200 ppm of host cell proteins, less than about 250 ppm of host cell proteins, less than about 150 ppm of host cell proteins, or less than about 100 ppm of host cell proteins. The amount of host cell proteins (e.g., in ppm), can be determined according to any suitable assay, including an ELISA such as a quantitative host cell protein ELISA. For example, the ppm of HCP are as measured by an ELISA assay.

In some aspects, the polypeptide of interest in the composition is an antibody or antibody construct. The antibody or antibody construct may have been expressed recombinantly by a transformed host cell (e.g., a host cell comprising a gene encoding the antibody or antibody construct), or may have been expressed via a hybridoma cell. The antibody or antibody construct may specifically bind to an epitope on TNF-like ligand 1A (TL1a). The antibody or antibody construct may specifically bind to an epitope on calcitonin gene-related peptide (CGRP). The antibody or antibody construct may specifically bind to an epitope on CD38.

In some aspects, the composition comprises a purified antibody or antibody construct that specifically binds to CGRP and comprises a heavy chain variable region and a light chain variable region. The heavy chain variable region (VH) may comprise the amino acid sequence of SEQ ID NO: 1. The light chain variable region (VL) may comprise the amino acid sequence of SEQ ID NO: 2. The composition may comprise an antibody or antibody construct comprising a VH comprising the amino acid sequence of SEQ ID NO: 1 and a VL, which antibody or antibody construct specifically binds to CGRP. The composition may comprise an antibody or antibody construct comprising a VL comprising the amino acid sequence of SEQ ID NO: 2 and a VH, which antibody or antibody construct specifically binds to CGRP. The composition may comprise an antibody or antibody construct comprising a VH comprising the amino acid sequence of SEQ ID NO: 1 and a VL comprising the amino acid sequence of SEQ ID NO: 2, which antibody or antibody construct specifically binds to CGRP. The antibody may be any antibody described in U.S. Publ. No. 2009/0220489 or PCT Publ. No. WO 2007/054809.

In some aspects, the composition comprises a purified antibody or antibody construct that specifically binds to TL1a and comprises a heavy chain variable region and a light chain variable region. The antibody may be any antibody described in U.S. Publ. No. 2014/0255302, which is incorporated by reference herein. The antibody may be any antibody described in U.S. Provisional Application. No. 62/220,442.

In some aspects, the composition comprises a purified antibody or antibody construct that specifically binds to CD38 and comprises a heavy chain variable region and a light chain variable region. The anti-CD38 antibody may further be fused to a second polypeptide molecule, for example, fused to a polypeptide toxin, or fused to an interferon polypeptide such as interferon alpha. The heavy chain variable region (VH) may comprise the amino acid sequence of SEQ ID NO: 3. The light chain variable region (VL) may comprise the amino acid sequence of SEQ ID NO: 4. The composition may comprise an antibody or antibody construct comprising a VH comprising the amino acid sequence of SEQ ID NO: 3 and a VL, which antibody or antibody construct specifically binds to CD38. The composition may comprise an antibody or antibody construct comprising a VL comprising the amino acid sequence of SEQ ID NO: 4 and a VH, which antibody or antibody construct specifically binds to CD38. The composition may comprise an antibody or antibody construct comprising a VH comprising the amino acid sequence of SEQ ID NO: 3 and a VL comprising the amino acid sequence of SEQ ID NO: 4, which antibody or antibody construct specifically binds to CD38. The antibody may be any antibody described in U.S. Publ. No. 2016/0068612 or in U.S. Publ. No. 2015/0313965, each of which are incorporated by reference herein, including antibodies that are further fused to an attenuated interferon molecule as described in these publications.

In some aspects, the composition comprises a purified antibody or antibody construct that specifically binds to TL1a and comprises a heavy chain variable region and a light chain variable region. The VH may comprise the amino acid sequence of SEQ ID NO: 5. The VH may comprise the amino acid sequence of SEQ ID NO: 6. The VL may comprise the amino acid sequence of SEQ ID NO: 7. Thus, the VH may comprise SEQ ID NO: 5 and the VL may comprise SEQ ID NO: 7, or the VH may comprise SEQ ID NO: 6 and the VL may comprise SEQ ID NO: 7. The composition may comprise an antibody or antibody construct comprising a VH comprising the amino acid sequence of SEQ ID NO: 5 or SEQ ID NO: 6 and a VL, which antibody or antibody construct specifically binds to TL1a. The composition may comprise an antibody or antibody construct comprising a VL comprising the amino acid sequence of SEQ ID NO: 7 and a VH, which antibody or antibody construct specifically binds to TL1a. The composition may comprise an antibody or antibody construct comprising a VH comprising the amino acid sequence of SEQ ID NO: 5 or SEQ ID NO: 6 and a VL comprising the amino acid sequence SEQ ID NO: 7, which antibody or antibody construct specifically binds to TL1a. The antibody may be any antibody described in U.S. application Ser. No. 15/267,213 or U.S. Publ. No. 2014/0255302, each of which are incorporated by reference herein.

In some preferred aspects, the antibodies (e.g., anti-TL1a, anti-CGRP, and anti-CD38) comprise a human IgG constant region. The human IgG constant region may be a human IgG1 or a human IgG4 constant region. The antibodies (e.g., anti-TL1a, anti-CGRP, and anti-CD38) may be humanized antibodies or fully human antibodies.

Host cell protein-reduced preparations of a protein of interest, including an antibody or antibody construct, that are produced according to a purification scheme that includes at least affinity chromatography that includes washing with an arginine-, sodium chloride-, and non-ionic or anionic surfactant-containing wash buffer as described herein, and which scheme optionally further includes one or more of a second chromatography purification step (e.g., AEX, AEX/HIC, CEX, or membrane chromatography), virus inactivation, nanofiltration, concentration, and diafiltration are also provided. Such host cell protein-reduced preparations include less than about 900 ppm of host cell proteins, less than about 800 ppm of host cell proteins, less than about 700 ppm of host cell proteins, less than about 600 ppm of host cell proteins, less than about 500 ppm of host cell proteins, less than about 450 ppm of host cell proteins, less than about 400 ppm of host cell proteins, less than about 350 ppm of host cell proteins, less than about 300 ppm of host cell proteins, less than about 200 ppm of host cell proteins, less than about 250 ppm of host cell proteins, less than about 150 ppm of host cell proteins, or less than about 100 ppm of host cell proteins. The amount of host cell proteins (e.g., in ppm), can be determined according to any suitable assay, including an ELISA such as a quantitative host cell protein ELISA. For example, the ppm of HCP are as measured by an ELISA assay.

Embodiments of the present disclosure can be further defined by reference to the following non-limiting examples, which describe in detail preparation of wash solutions of the present disclosure and methods for using wash solutions of the present disclosure for the purification of proteins of interest. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

Materials and Methods

Material and Equipment. Monoclonal antibodies used in these Examples were expressed in-house using Chinese Hamster Ovary (CHO) cells. MABSELECT SURE® Protein A resin was purchased from GE Healthcare (Uppsala, Sweden). All buffer solutions were prepared using ultrapure water obtained from a Millipore water purification system. Chemicals used for buffer and solution preparation were obtained from JT Baker (Philipsburg, N.J.). High throughput chromatographic experiments were carried out on a Tecan Freedom EVO® 200 liquid handling system (Tecan Group AG, Mannedorf Switzerland). This instrument has a built-in resin plate and Atoll column station allowing for a maximum of 96 chromatography conditions being studied in parallel. FREEDOM EVOWARE® software (Tecan Group AG, Mannedorf Switzerland) was used for system control and sample collection. Selected wash solutions from the high throughput study were further verified using an Akta Avant liquid chromatography system (GE Healthcare Life Sciences, Uppsala, Sweden). This instrument has a built-in UV and conductivity detector to monitor the outlet of the column allowing one wash condition being studied per run.

Protein A Chromatography. The MABSELECT SURE® chromatography column was equilibrated with 1×PBS for 5 C.V (column volume). After equilibration, the harvested cell culture fluid (HCCF) was loaded onto the column at a load capacity of 40 grams of mAb per liter of resin. Following load application, the column was first washed with 3 column volumes (CV) 1×PBS buffer, followed by a second wash with 5 CV of the candidate wash buffer. The column was subsequently washed with a third wash using 5 CV 5 mM Succinic Acid pH 5.8 buffer. The mAb was eluted from the column using 5CV 25 mM Glycine, 10 mM Succinic Acid, pH 3.7 buffer. The cleaning in place was applied after production.

Quantitative ELISA—host cell protein (HCP). Host Cell Protein (HCP) was determined by the CHO Host Cell Proteins 3rd Generation kit (Immunoenzymetric Assay for the Measurement of CHO Host Cell Proteins, Catalog # F550, Cygnus Technologies, Southport, N.C.) following manufacturer's protocol. The absorbance data at 450/650 nm were acquired on the SPECTRAMAX® Plus microplate reader (Molecular Devices, Sunnyvale Calif.) and analyzed with SOFTMAX® Pro 6.4.2 software (Molecular Devices, Sunnyvale, Calif.). HCP values were calculated from a four parameter logistic fit of the standard curves generated from the standards included in the CHO Host Cell Proteins 3rd Generation kit.

Example 2

Experimental Results from Plate Based Study

A total of 28 single component conditions were studied for HCP clearance using a TL1a antibody in Mab Select SuRe resin plate. The results are presented in FIG. 1 and can be summarized as follows.

Compared with sodium octanoate (CA) and surfactants, amino acids and tetramethylammonium chloride (TMAC) are more effective in HCP clearance.

There is a trend of increased HCP clearance with increased concentration of amino acids or TMAC; the same is true for CA in the concentration range tested.

Arginine and guanidine are most effective amongst all the chemicals tested.

Figure 2:
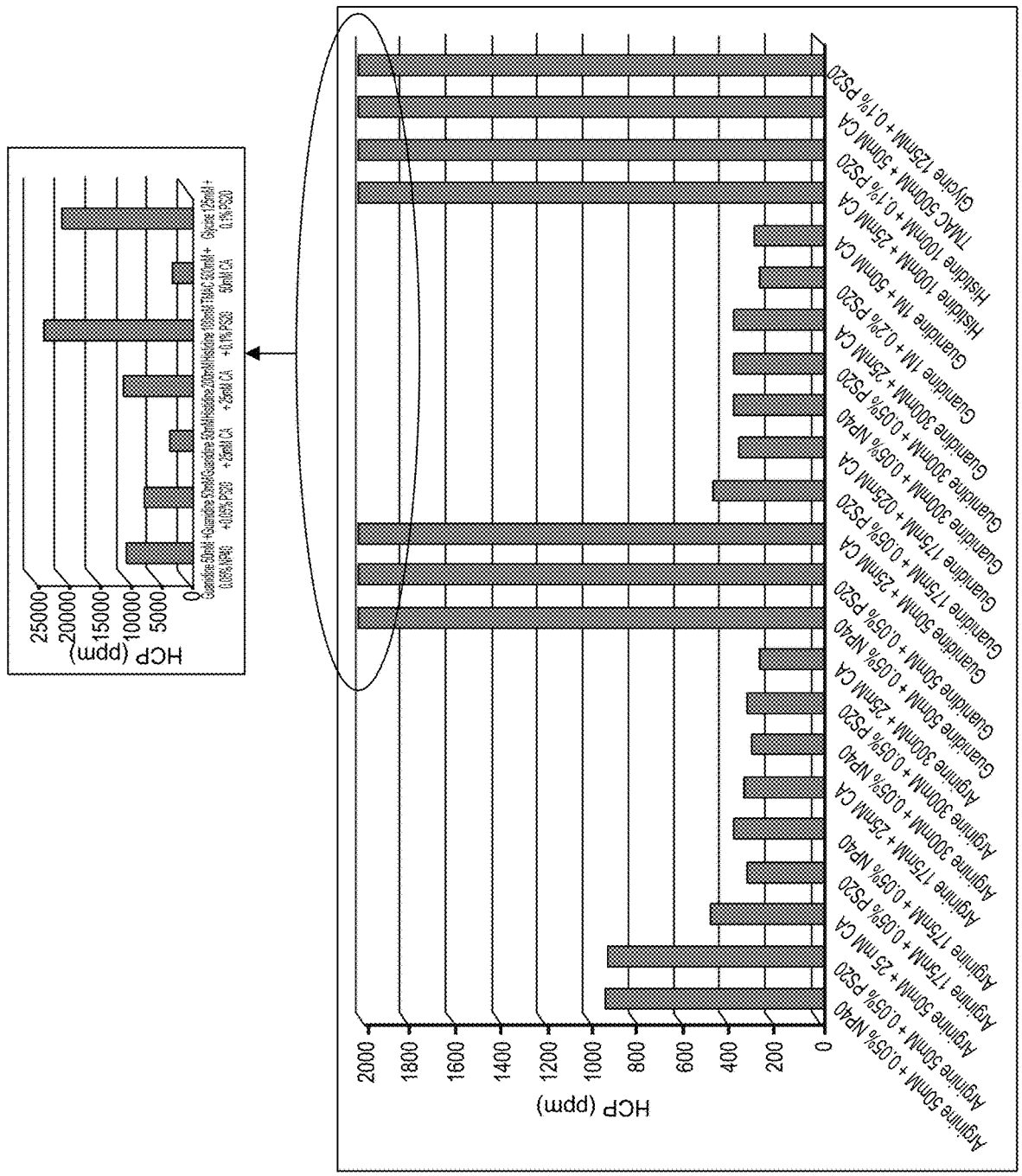
FIG. 2 shows HCP removal by wash buffers comprising a combination of an amino acid and a surfactant, or a combination of guanidine and a surfactant in resin plate.

The dual component HCP clearance results are presented in FIG. 2. In the dual component experiments, a detergent and a charged excipient, including arginine, guanidine, histidine, TMAC or glycine, are combined to evaluate effectiveness for HCP clearance. The results can be summarized as follows.

Adding 25 mM CA into low concentration of charged excipients (either 50 mM arginine or 50 mM guanidine or 100 mM Histidine) can significantly improve HCP clearance compared with adding 0.05% w/v NP 40 or 0.05% w/v PS 20.

When arginine or guanidine concentration is above 175 mM, specifically when arginine is tested in the range of 175 mM to 300 mM, and guanidine in the range of 175 mM to 1 M, HCP clearance to below 500 ppm is achieved for all dual component combinations tested.

Figure 3:
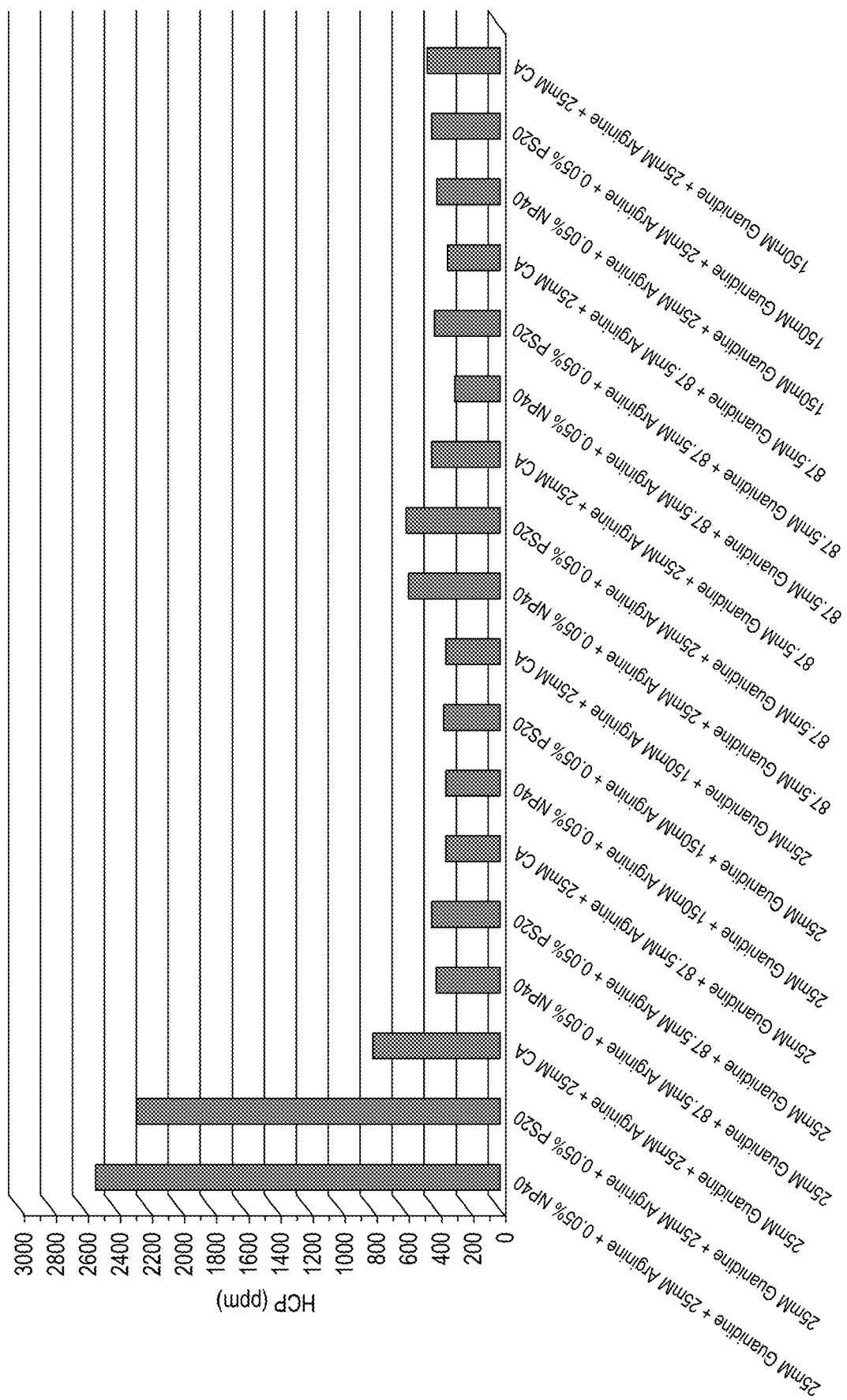
FIG. 3 shows HCP removal by wash buffers comprising a combination of arginine and guanidine with a surfactant in resin plate.

In tri-component screen, the combined effect of arginine, guanidine and a detergent is tested and the HCP clearance results are presented in FIG. 3. The results can be summarized as follows.

It is possible to achieve HCP clearance to <500 ppm with low concentrations of guanidine and arginine, each at <100 mM, in combination with a detergent.

Adding 25 mM CA into low concentration of arginine and guanidine combination (arginine and guanidine each at <100 mM) improves HCP clearance compared with adding 0.05% w/v NP 40 or 0.05% w/v PS 20.

When the combined guanidine and arginine concentration is >175 mM, HCP clearance is consistently <500 ppm.

Example 3

Experimental Results from Atoll Column

Figure 4:
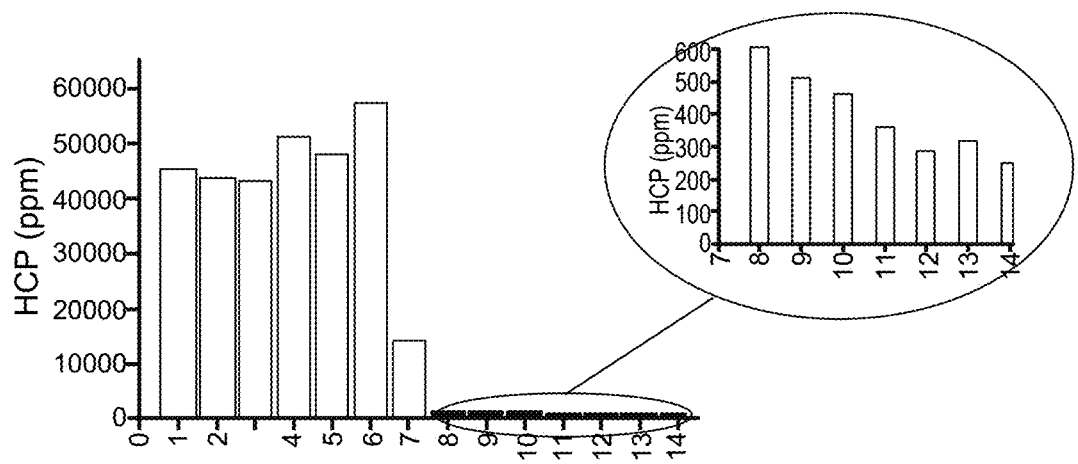
FIG. 4 shows the HCP removal by combinations of NaCl, Tributyl phosphate, TRITON® X-100, arginine, sodium octanoate and guanidine in an Atoll column.

Fourteen wash solutions were investigated for their HCP clearance for anti-T11a (mAb) on MABSELECT SURE® Chromatography (GE Healthcare Life Sciences, Uppsala, Sweden). HCP levels in the elution pool are shown in FIG. 4. The results can be summarized as follows.

The seven non-arginine or non-guanidine containing wash solutions had a HCP level over 10,000 ppm.

When using 250 mM arginine alone, HCP clearance is about 400-500 ppm; when 0.05% w/v tributyl phosphate and 150 mM NaCl are introduced, arginine concentration can be reduced to 200 mM with an improvement of HCP clearance to 300-400 ppm. This strategy has a cost benefit since arginine is expensive.

When 0.1% w/v TRITON® X-100 is combined with 250 mM arginine and 150 mM NaCl, HCP is reduced to 200-300 ppm.

With the application of guanidine with 150 mM NaCl, HCP clearance can be reduced to 500-600 ppm.

When 250 mM arginine is combined with 25 mM CA and 150 mM NaCl, HCP is reduced to around 300 ppm. When 150 mM arginine is replaced with 150 mM guanidine, HCP clearance remains at around 300 ppm. This strategy has cost benefit because arginine is more expensive than guanidine.

In a summary, four combined solutions demonstrated better HCP clearance compared with single component or dual-component solutions.

200 mM arginine, 0.05% w/v tributyl Pi, 150 mM NaCl
250 mM arginine, 25 mM CA, 150 mM NaCl
100 mM arginine, 150 mM guanidine, 25 mM CA, 150 mM NaCl
0.1% w/v TRITON® X-100, 250 mM arginine, 150 mM NaCl For condition 250 mM arginine, 25 mM CA, 150 mM NaCl, replace 150 mM arginine with guanidine is equal effective in HCP clearance and less expensive.

Figure 5:
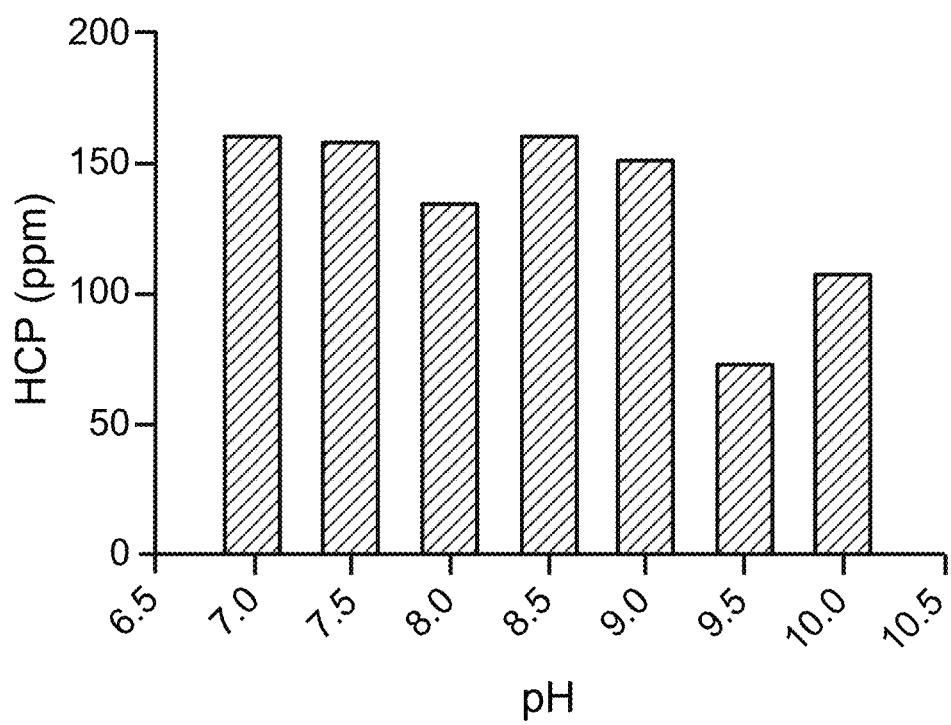
FIG. 5 shows the influence of pH on host cell protein clearance using the TRITON® X-100 non-ionic surfactant/NaCl/arginine wash buffer.

The wash solution containing 250 mM arginine, 0.1% w/v TRITON® X-100 non-ionic surfactant and 150 mM NaCl was further investigated for its HCP clearance under multiple pH values using anti-T11a antibodies as a model. The results are presented in FIG. 5. In the pH range from 6.5 to pH 10.5, HCP level in the elution pool ranged from 100 ppm to 200 ppm, and no significant pH impact was observed. It is believed that 150 mM NaCl is enough to shield all charge groups on the proteins. Therefore, pH was not observed to have any significant effect. All combined solutions contain 150 mM NaCl and pH effect is not further tested.

Figure 6:
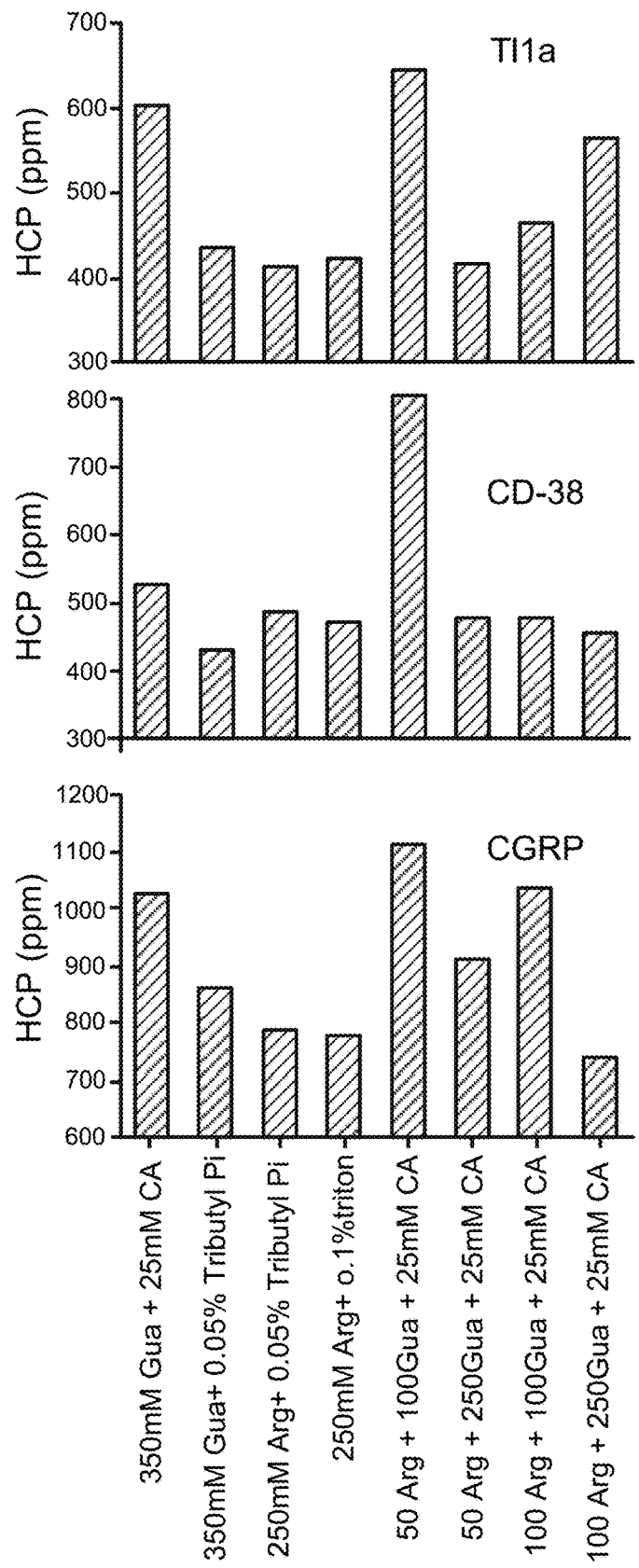
FIG. 6 shows the HCP removal from different antibodies (anti-TL1a, anti-CD-38 and anti-CGRP) using a wash with various combinations of arginine, guanidine, surfactant and sodium octanoate.

The combination of arginine with 0.1% w/v TRITON® X-100, the combination of arginine with guanidine and sodium octonoate, and the combination of tributyl phosphate were studied with anti-TL1a antibody, anti-calcitonin gene-related peptide (CGRP) antibody and a fusion protein which was a monoclonal anti-CD38 antibody fused at its C-terminus to an interferon molecule. HCP clearance results are presented in FIG. 6. The combinations that are effective for all three molecules are 250 mM arginine+0.1% w/v TRITON® X-100 (or +0.05% w/v tributyl phosphate)
50-100 mM arginine+100-250 mM Gu+25 mM CA, preferably with >50 mM arginine, and with >100 mM guanidine
350 mM guanidine+0.05% w/v tributyl phosphate This data suggests that these wash solutions can be used in a platform process, i.e. they would be expected to be effective in the purification of any antibody.

Example 4

Concentration Effects

The effect of TRITON® X-100 nonionic surfactant, arginine and NaCl concentration on HCP clearance were also investigated with anti-TL1a, anti-CGRP, and anti-CD38-IFN fusion molecules. Eight wash solutions were studied, and HCP results are summarized in Table 1. These data show similar trends for all three molecules, in terms of HCP clearance. The data showed that a wash of 0.15% w/v TRITON® X-100 non-ionic surfactant, 300 mM arginine and 100 mM NaCl provided significant improvements in terms of HCP removal. The effective HCP clearance working range for TRITON® X-100 is 0.05%-0.15% w/v, for arginine is 200-300 mM and NaCl is 100-200 mM. The data suggests that these wash solutions would be effective in the purification of any peptide of interest (e.g., antibody).

TABLE 1

The effects of additive concentration (TRITON ® X-100, arginine, NaCl) on HCP clearance for anti-TL1a, anti-CGRP, and anti-CD38-IFN fusion proteins.

| TRITON ® X-100 (% w/v) | Arginine (mM) | NaCl (mM) | HCP (ppm) | | |
|---|---|---|---|---|---|
| | | | αTL1a | αCGRP | αCD38 |
| 0.05 | 200 | 200 | 246 | 852 | 503 |
| 0.15 | 250 | 200 | 253 | 707 | 301 |
| 0.1 | 200 | 100 | 245 | 711 | 384 |
| 0.1 | 250 | 150 | 244 | 627 | 153 |
| 0.1 | 300 | 200 | 247 | 665 | 353 |
| 0.05 | 300 | 150 | 183 | 629 | 304 |
| 0.05 | 250 | 100 | 265 | 602 | 336 |
| 0.15 | 300 | 100 | 152 | 557 | 97 |
| 0.15 | 200 | 150 | 521 | 556 | 497 |

TABLE 2

The effects of additive concentration (arginine, guanidine, sodium octonoate, NaCl) on HCP clearance for anti-TL1a, anti-CGRP, and anti-CD38-IFN fusion proteins.

| Arginine (mM) | Guanidine (mM) | Sodium Octanoate (mM) | NaCl (mM) | HCP (ppm) | | |
|---|---|---|---|---|---|---|
| | | | | αTL1a | αCGRP | αCD38 |
| 50 | 50 | 5 | 0 | 703 | 1,336 | 295 |
| 100 | 150 | 25 | 150 | 278 | 785 | 234 |
| 150 | 250 | 45 | 0 | 245 | 628 | 182 |
| 50 | 250 | 45 | 300 | 248 | 844 | 213 |
| 150 | 50 | 5 | 300 | 300 | 1,265 | 381 |
| 150 | 250 | 5 | 0 | 270 | 681 | 212 |
| 50 | 50 | 45 | 0 | 471 | 898 | 270 |
| 150 | 50 | 45 | 300 | 306 | 692 | 249 |

Example 5

Process Verification of Selected Conditions

Four process conditions were further studied with three molecules (TL1a, CGRP and CD-38) on 5-cm chromatography column with Mab Select SuRe and Sartobind Q process. HCP clearance results were summarized in Table 3. All 3 combined wash conditions showed substantial improvement in HCP removal relative to control condition 1 M NaCl. The residual HCPs after Protein A and Sartobind Q step are low which meet clinical use requirement (HCP<100 ppm)

TABLE 3

Process verification for three molecules on selected conditions-HCP (ppm)

| Molecules | | 100 mM Arginine, 150 mM Guanidine, 25 mM CA, 150 mM NaCl | 200 mM Arginine, 0.05% w/v Tributyl, 150 mM NaCl | 250 mM Arginine, 150 mM NaCl, 0.1% w/v TRITON ® X-100 | Control 1M NaCl |
|---|---|---|---|---|---|
| TL1a | ProA | 241 | 265 | 190 | 20,940 |
| | SartoQ | 26 | 21 | 21 | N/A |
| CGRP | ProA | 473 | 484 | 212 | 1,025 |
| | SartoQ | 59 | 43 | 43 | N/A |

TABLE 3-continued

Process verification for three molecules on selected conditions-HCP (ppm)

| Molecules | | 100 mM Arginine, 150 mM Guanidine, 25 mM CA, 150 mM NaCl | 200 mM Arginine, 0.05% w/v Tributyl, 150 mM NaCl | 250 mM Arginine, 150 mM NaCl, 0.1% w/v TRITON® X-100 | Control 1M NaCl |
|---|---|---|---|---|---|
| CD-38 | ProA | 532 | 550 | 268 | 749 |
|  | SartoQ | 58 | 56 | 37 | N/A |

Example 6

Viral Clearance Results

Seven selected wash solutions were studied the viral clearance for In-vitro Viral-Like particles clearance and results are summarized in Table 4A. TRITON® X-100 was observed highly effective in in vitro VLP clearance.

TABLE 4A

In-vitro Viral-like Particle Clearance

| Wash Condition | LRV |
|---|---|
| 0.1% w/v TRITON® X-100 | 3.85 |
| 150 mM NaCl | 1.73 |
| 250 mM Arginine | 1.82 |
| 25 mM CA | 1.57 |
| 0.1% w/v TRITON® X-100, 250 mM Arginine, and 150 mM NaCl | 4.43 |
| 25 mM CA, 250 mM Arginine, and 150 mM NaCl | 2.04 |
| 100 mM Arginine, 150 mM Guanidine, 150 mM NaCl, and 25 mM CA | 1.21 |

Studies using additional wash solutions (summarized in Table 4B) showed that Triton can significantly improve Retrovirus-like particle clearance.

TABLE 4B

Retrovirus-like Particle Clearance from Different Surfactants

| Wash Condition | LRV |
|---|---|
| 0.1% TRITON® X-100, 20 mM Tris, pH 7.5 | 3.54 |
| 0.05% TRITON® X-100, 20 mM Tris, pH 7.5 | 3.06 |
| 0.1% PS 80, 20 mM Tris, pH 7.5 | 0.86 |
| 0.1% PS 20, 20 mM Tris, pH 7.5 | 1.05 |
| 50 mM CA, 20 mM Tris, pH 7.5 | 0.93 |
| 0.05% TNBP, 20 mM Tris, pH 7.5 | 0.84 |
| 5 mM Succinic acid, pH 5.8 | 0.85 |

Furthermore, viral clearance from selected wash solutions was assessed by using two model virus: xenotropic murine leukemia virus (X-MulV) and minute virus of mice (MVM) by spike-in study. The compositions and results are shown in Tables 5 and 6. The results show that, compared with the control wash solution of 5 mM succinic acid at pH 5.8, there was a 1.7-log (arginine) or 0.8-log (arginine+guanidine) improvement in X-MulV clearance and a 1.0-log (arginine+tributyl phosphate) or a 1.3-log (arginine) or (arginine+guanidine) improvement in MVM clearance.

TABLE 5

Spike-in Viral Clearance Study

| | | Log10 Reduction Value | |
|---|---|---|---|
| Process Step | | X-MuLV | MVM |
| MabSelect SuRe Wash | 250 mM Arginine, 0.1% w/v TRITON® X-100, 150 mM NaCl, pH 7.5 | 5.86 | 3.08 |
| | | 4.78 | 3.03 |
| | 5 mM Succinic Acid, pH 5.8 control | 3.07 | 1.77 |
| | 100 Arginine + 150 Guanidine + 25 mM Sodium Caprylate + 150 mM NaCl, pH 7.5 | 3.84 | 3.05 |

TABLE 6

Spike-in Viral Clearance Study

| | Log10 Reduction Value | |
|---|---|---|
| Process Step | X-MuLV | MVM |
| 200 mM Arginine, 0.05% Tributyl Phosphate, 150 mM NaCl | 3.8 | 2.4 |
| 5 mM Succinic Acid Control | 2.7 | 1.7 |

The invention is not limited to the embodiments described and exemplified above, but is capable of variation and modification within the scope of the appended claims.

Various publications, including patents, patent applications, accession numbers, technical articles and scholarly articles are cited throughout the specification. Each of these cited publications is incorporated by reference herein, in its entirety and for all purposes.

```
Sequence Listing
Anti-CGRP VH
                                                         (SEQ ID NO: 1)
    1 EVQLVESGGG LVQPGGSLRL SCAASGFTFS NYWISWVRQA PGKGLEWVAE      50

51 IRSESDASAT HYAEAVKGRF TISRDNAKNS LYLQMNSLRA EDTAVYYCLA     100

101 YFDYGLAIQN YWGQGTLVTV SS

Anti-CGRP VL
                                                         (SEQ ID NO: 2)
    1 EIVLTQSPAT LSLSPGERAT LSCKASKRVT TYVSWYQQKP GQAPRLLIYG      50
```

-continued

```
 51 ASNRYLGIPA RFSGSGSGTD FTLTISSLEP EDFAVYYCSQ SYNYPYTFGQ    100

101 GTKLEIK

Anti-CD38 VH
                                                  (SEQ ID NO: 3)
  1 EVQLVQSGAE VKKPGATVKI SCKVSGYTFT DSVMNWVQQA PGKGLEWMGW    50

51 IDPEYGRTDV AEKFQGRVTI TADTSTDTAY MELSSLRSED TAVYYCARTK   100

101 YNSGYGFPYW GQGTTVTVSS

Anti-CD38 VL
                                                  (SEQ ID NO: 4)
  1 DIQMTQSPSS LSASVGDRVT ITCKASQNVD SDVDWYQQKP GKAPKLLIYK    50

51 ASNDYTGVPS RFSGSGSGTD FTFTISSLQP EDIATYYCMQ SNTHPRTFGG   100

101 GTKVEIKR

Anti-TL1a VH1
                                                  (SEQ ID NO: 5)
QVQLVQSGAEVKKPGASVKVSCKASGYTFTSYDINWVRQAPGQGLEWMGWLNPNSGNTGY

AQKFQGRVTMTADRSTSTAYMELSSLRSEDTAVYYCAREVPETAAFEYWGQGTLVTVSS

Anti-TL1a VH2
                                                  (SEQ ID NO: 6)
QVQLVQSGAEVKKPGASVKVSCKASGYTFTSYDINWVRQAPGQGLEWMGWLNPNSGYTGY

AQKFQGRVTMTADRSTSTAYMELSSLRSEDTAVYYCAREVPETAAFEYWGQGTLVTVSS

Anti-TL1a VL
                                                  (SEQ ID NO: 7)
QSVLTQPPSVSGAPGQRVTISCTSSSSDIGAXXGVXWYQQLPGTAPKLLIEGYYNRPSGVPDRF

SGSKSGTSASLTITGLLPEDEGDYYCQSXDGTLSALFGGGTKLTVLG

Xaa 32 is G or A
Xaa 33 is L or S or Q
Xaa 36 is H or L
Xaa 93 is Y or F or W
```

---

What is claimed is:

1. A method of preparing a purified protein of interest, comprising loading a mixture comprising a protein of interest and one or more contaminant proteins onto an affinity chromatography ligand, washing the ligand with an aqueous wash solution comprising arginine and guanidine to elute the one or more contaminant proteins from the ligand, and then eluting the protein of interest from the ligand, thereby forming a purified eluate of the protein of interest, wherein the protein of interest is an antibody.

2. The method according to claim 1, wherein the affinity chromatography ligand comprises Protein A.

3. The method of claim 1, further comprising lowering the pH of the purified eluate of the protein of interest for a period of time sufficient to inactivate viruses.

4. The method of claim 1, further comprising filtering the purified eluate of the protein of interest to remove viruses.

5. The method of claim 1, further comprising loading the purified eluate of the protein of interest onto a membrane chromatography support and collecting flow through comprising a further-purified eluate from the membrane chromatography support.

6. The method of claim 1, further comprising formulating the purified eluate of the protein of interest as a composition including a pharmaceutically acceptable excipient.

7. The method according to claim 5, further comprising formulating the further-purified eluate of the protein of interest as a composition including a pharmaceutically acceptable excipient.

8. The method of claim 2 wherein the aqueous wash solution increases viral clearance from the mixture as measured by a virus log reduction value (LRV).

9. The method of claim 1, wherein the solution comprises: greater than 0 mM and less than about 200 mM arginine and from about 50 mM to about 250 mM guanidine.

10. The method of claim 9, wherein the solution comprises from about 50 mM to about 150 mM arginine.

11. The method of claim 9, wherein the solution comprises from about 75 mM to about 125 mM arginine.

12. The method of claim 9, wherein the solution comprises from about 100 mM guanidine to about 200 mM guanidine.

13. The method of claim 9, wherein the solution comprises from about 150 mM guanidine to about 200 mM guanidine.

14. The method of claim 1, wherein the combined guanidine and arginine concentration is >175 mM.

15. The method of claim 9, wherein the combined guanidine and arginine concentration is >175 mM.

16. The method of claim 9, wherein the solution comprises 50-100 mM arginine, 100-250 mM guanidine, and 25 mM sodium octanoate.

17. The method of claim 1, wherein the solution further comprises an anionic surfactant.

18. The method of claim 17, wherein the anionic surfactant comprises sodium octanoate.

19. The method of claim 1, wherein the solution further comprises sodium chloride.

20. The method of claim 1, wherein the solution comprises a pH of about 7.5.

\* \* \* \* \*

SEQUENCE LISTING

<160> NUMBER OF SEQ ID NOS: 7

<210> SEQ ID NO 1
<211> LENGTH: 122
<212> TYPE: PRT
<213> ORGANISM: Artificial Sequence
<220> FEATURE:
<223> OTHER INFORMATION: Anti-CGRP VH

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110
```

```
Gly Gln Gly Thr Leu Val Thr Val Ser Ser
        115                 120
```

<210> SEQ ID NO 2
<211> LENGTH: 107
<212> TYPE: PRT
<213> ORGANISM: Artificial Sequence
<220> FEATURE:
<223> OTHER INFORMATION: Anti-CGRP VL

<400> SEQUENCE: 2

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105
```

<210> SEQ ID NO 3
<211> LENGTH: 120
<212> TYPE: PRT
<213> ORGANISM: Artificial Sequence
<220> FEATURE:
<223> OTHER INFORMATION: Anti-CD38 VH

<400> SEQUENCE: 3

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 4
<211> LENGTH: 108
<212> TYPE: PRT
<213> ORGANISM: Artificial Sequence
<220> FEATURE:
<223> OTHER INFORMATION: Anti-CD38 VL

<400> SEQUENCE: 4

```
Asp Ile Gln Met Thr Gln Ser Pro Ser Ser Leu Ser Ala Ser Val Gly
```

```
              1               5                  10                 15
Asp Arg Val Thr Ile Thr Cys Lys Ala Ser Gln Asn Val Asp Ser Asp
                          20                  25                  30

Val Asp Trp Tyr Gln Gln Lys Pro Gly Lys Ala Pro Lys Leu Leu Ile
            35                  40                  45

Tyr Lys Ala Ser Asn Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
                100                 105
```

<210> SEQ ID NO 5
<211> LENGTH: 119
<212> TYPE: PRT
<213> ORGANISM: Artificial Sequence
<220> FEATURE:
<223> OTHER INFORMATION: Anti-TL1a VH1

<400> SEQUENCE: 5

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
                100                 105                 110

Thr Leu Val Thr Val Ser Ser
        115
```

<210> SEQ ID NO 6
<211> LENGTH: 119
<212> TYPE: PRT
<213> ORGANISM: Artificial Sequence
<220> FEATURE:
<223> OTHER INFORMATION: Anti-TL1a VH2

<400> SEQUENCE: 6

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 7
<211> LENGTH: 111
<212> TYPE: PRT
<213> ORGANISM: Artificial Sequence
<220> FEATURE:
<223> OTHER INFORMATION: Anti-TL1a VL
<220> FEATURE:
<221> NAME/KEY: MISC_FEATURE
<222> LOCATION: (32)..(32)
<223> OTHER INFORMATION: Xaa is G or A
<220> FEATURE:
<221> NAME/KEY: MISC_FEATURE
<222> LOCATION: (33)..(33)
<223> OTHER INFORMATION: Xaa is L, S or Q
<220> FEATURE:
<221> NAME/KEY: MISC_FEATURE
<222> LOCATION: (36)..(36)
<223> OTHER INFORMATION: Xaa is H or L
<220> FEATURE:
<221> NAME/KEY: MISC_FEATURE
<222> LOCATION: (93)..(93)
<223> OTHER INFORMATION: Xaa is Y, F or W

<400> SEQUENCE: 7

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Xaa
            20                  25                  30

Xaa Gly Val Xaa Trp Tyr Gln Gln Leu Pro Gly Thr Ala Pro Lys Leu
            35                  40                  45

Leu Ile Glu Gly Tyr Tyr Asn Arg Pro Ser Gly Val Pro Asp Arg Phe
        50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Xaa Asp Gly Thr
                85                  90                  95

Leu Ser Ala Leu Phe Gly Gly Gly Thr Lys Leu Thr Val Leu Gly
            100                 105                 110
```